United States Patent [19]
Siiman et al.

[11] Patent Number: 5,552,086
[45] Date of Patent: Sep. 3, 1996

[54] IMMOBILIZED METAL COLLOIDS ON DISPERSED POLYMER MICROSPHERES

[75] Inventors: Olavi Siiman, Davie; Alexander Burshteyn, Hialeah; Marilyn Cayer, Miami, all of Fla.

[73] Assignee: Coulter Corporation, Miami, Fla.

[21] Appl. No.: 118,980

[22] Filed: Sep. 9, 1993

Related U.S. Application Data

[63] Continuation-in-part of Ser. No. 827,347, Jan. 29, 1992, Pat. No. 5,248,772.

[51] Int. Cl.$^6$ .............................. B01J 13/22; B32B 15/08; B32B 15/16; G01N 33/52

[52] U.S. Cl. .................... 252/408.1; 252/315.2; 427/213.31; 427/214; 428/402.24; 428/403; 428/407

[58] Field of Search .............................. 252/315.2, 408.1; 428/402.24, 403, 407, 461, 493; 427/2.23, 213.31, 214; 436/170; 424/9.1

[56] References Cited

U.S. PATENT DOCUMENTS

| | | | |
|---|---|---|---|
| 4,123,396 | 10/1978 | Rembaum et al. | 526/44 |
| 4,452,773 | 6/1984 | Molday | 424/1.1 |
| 4,624,923 | 11/1986 | Margel | 428/407 X |
| 4,665,020 | 5/1987 | Saunders | 424/7.1 X |
| 4,879,220 | 11/1989 | Mrsny et al. | 424/7.1 X |
| 5,169,754 | 12/1992 | Siiman et al. | 428/407 X |
| 5,213,895 | 5/1993 | Hirai et al. | 428/403 |
| 5,240,640 | 8/1993 | Siiman et al. | 252/315.2 |
| 5,248,772 | 9/1993 | Siiman et al. | 424/7.1 X |

*Primary Examiner*—Richard D. Lovering
*Attorney, Agent, or Firm*—Michelle A. Kaye

[57] ABSTRACT

The invention describes stable colloidal polymeric particles of 0.2–5.0 microns size which are coated with a first aminodextran layer and a second metallic solid layer, The metal is coated by reduction of a metallic salt or complex by the aminodextran. The metal coated particles, which preferably are gold- or silver-coated polymeric microspheres, produce side scatter and forward shifts in flow cytometry applications that are in agreement with the theoretical shifts predicted for solid gold or silver spheres of similar size in flow cytometry applications,

35 Claims, 24 Drawing Sheets

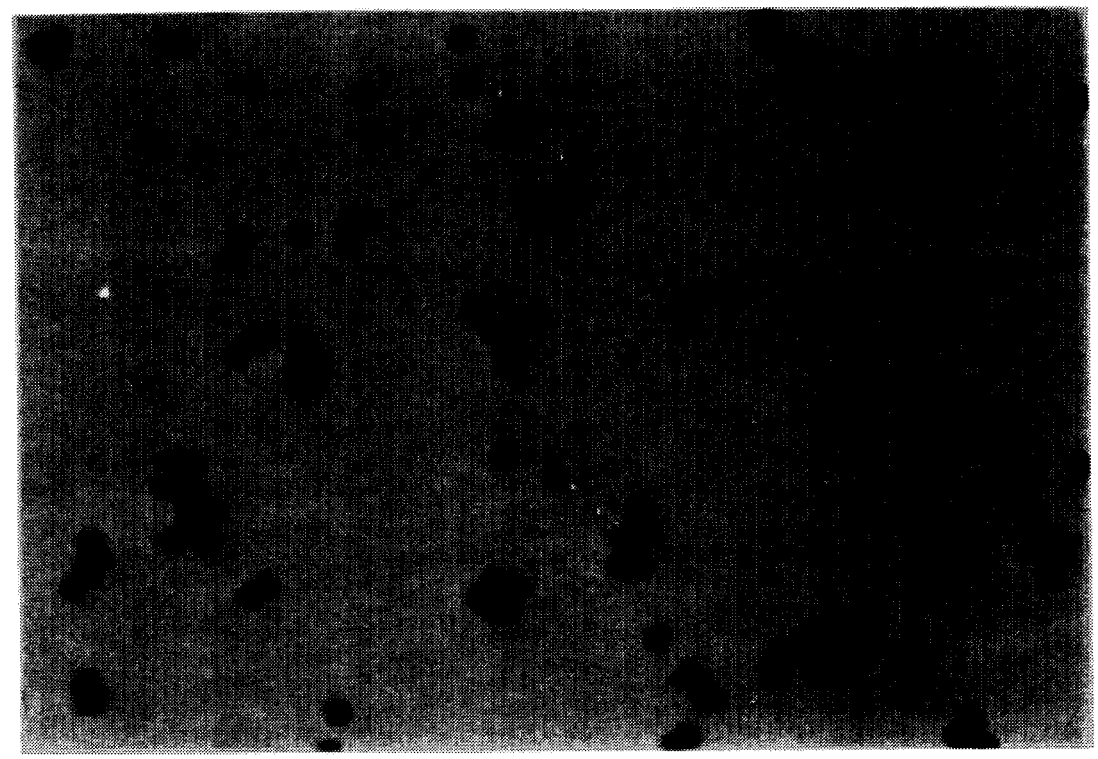
FIG. IA
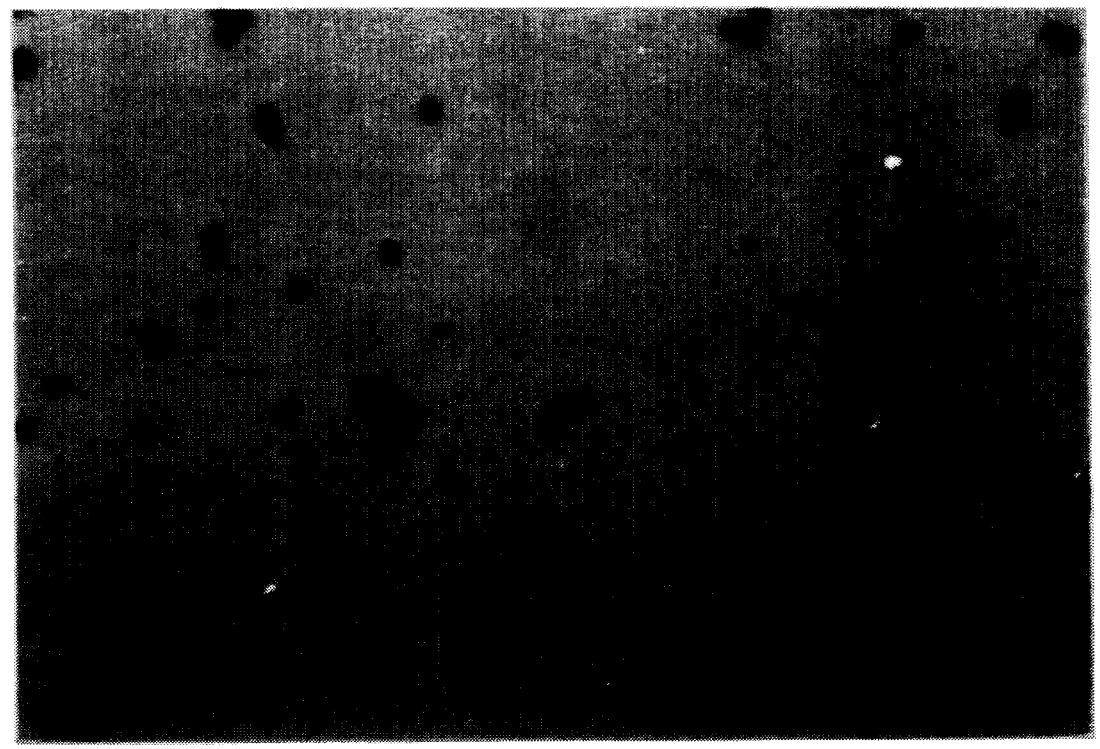
FIG. IB

IMMOBILIZED METAL COLLOIDS ON DISPERSED POLYMER MICROSPHERES

RELATED INVENTIONS

This application is a Continuation-In-Part of U.S. Pat. No. 5,248,772, issued on Sep. 28, 1993, and entitled FORMATION OF COLLOIDAL METAL DISPERSIONS USING AMINODEXTRANS AS REDUCTANTS AND PROTECTIVE AGENTS; and is related to application Ser. No. 08/336,725, filed Nov. 9, 1994, which is a Continuation of application Ser. No. 07/961,157, filed Oct. 15, 1992 and entitled POLYMERIC PARTICLES HAVING A BIODEGRADABLE GELATIN OR AMINODEXTRAN COATING AND PROCESS FOR MAKING SAME, now Abandoned, which in turn is a Continuation-In-Part of U.S. Pat. No. 5,169,754, issued Dec. 8, 1992, and entitled, BIODEGRADABLE PARTICLE COATINGS HAVING A PROTEIN COVALENTLY IMMOBILIZED BY MEANS OF A CROSSLINKING AGENT AND PROCESS FOR MAKING SAME. This application and the above applications and patents are commonly owned by a single assignee, Coulter Corporation, Miami, Fla.

FIELD OF THE INVENTION

This invention relates generally to a method for preparing stable colloidal particles having a thin layer of a selected metal deposited thereon and the particles prepared by this method. In particular, the invention is directed to a method of preparing discrete, metal coated colloidal particles using an aminodextran. The aminodextran is coated on a particulate substrate and the aminodextran-coated substrate is contacted with a solution containing a metal salt or complex in which the metal is capable of being reduced from the ionic state to the zero valent state by the aminodextran.

BACKGROUND OF THE INVENTION

The use of colloidal particles and magnetic particles to bind a compound has long been known and used in industrial and laboratory procedures. For example, crosslinked polystyrene-divinylbenzene beads, among the earliest and most widely used particles, have been used in organic synthesis, catalysis and the biotechnical arts, especially immunology. In combination with the appropriate reagents, the particles have been used to remove specific cells from a sample containing a plurality of cell types or to enhance the results of instrumental biomedical assays. For example, polystyrene microbeads have been used as a standard in place of natural cells in order to reduce test-to-test variances. Unless specified otherwise, the terms "particles", "spheroids", "spheres", "microspheres" and "beads" as used herein, are interchangeable.

In the 1970s, there emerged a phenomena known as SERS or Surface-Enhanced Raman Scattering [9,10]. Using thin metal films or coatings deposited on a substrate, it was found that small structures of conducting metals such as gold or silver showed unusual light scattering and absorption effects; provided that the structures had dimensions about that or smaller than the wavelength of the exciting radiation being used. These effects were found to be due to the unique refractive index versus wavelength properties of such structures. Various methods have been developed for depositing metal coatings on various substrates. However, achieving a uniform metal coating has been difficult, especially on three-dimensional substrates like polymeric or glass beads.

The preparation of gold- and silver-coated substrates, including spheroidal particles, has been described in numerous publications. In the early stages of this art, Teflon® spheres on a flat glass surface were coated with silver structures or "bumps" of 100–200 nm (nanometers) diameter and 75–80 nm thickness [1]. The silver metal was deposited using well known vapor deposition techniques. Raman spectroscopy of organic substances adsorbed on the silver surfaces showed that there was enhanced Raman scattering relative to standard techniques. Metal vapor deposition has also been the standard method of applying thin gold coatings onto samples prepared for scanning electron microscopy (SEM) [2]. In both these instances, the particles were not entirely coated with the selected metal because the particulate samples were supported by some substrate. For example, the particles were scattered on a glass slide before vapor deposition of the metal. The portion or area of the particle in contact with the substrate was thus shielded from the coating vapor. The vapor deposition technique might better be used with aerosols, provided that the particles prepared would be large enough to scatter light and would remain suspended after coating with a heavy metal. Regardless, one can conclude that the vapor deposition technique would not be representative of metal coated spheres prepared in situ in solution and transferred into a liquid system to yield a colloidal suspension of uniformly coated particles.

Heterocoagulation methods using polymer spheres and based on established procedures [3,4] for the formation of gold or silver hydrosols have been studied by the present inventors. When using amidine or sulfate polystyrene particles or latices as the substrate in an aqueous medium, no detectable amounts of metal were deposited on the substrate. Instead, using gold hydrosols and polystyrene particles, as an example, separate colloidal gold metal particles of about 20 nm diameter were formed in the aqueous medium. Thus, there existed separate and distinct gold and polystyrene particles. Extinction spectra indicated that not even small gold bumps, analogous to the silver bumps or of smaller size, were deposited on the polystyrene particles. The technical literature, however, contains some reports of the deposition of certain metal compounds on polymer microspheres using heterocoagulation techniques [5,6; yttrium, aluminum, zirconium and chromium were reported deposited]. S. Margel reported the deposition of transition metals, including gold and silver, on polyaldehyde microspheres [8]. An aqueous suspension of microspheres in a metal ion containing solution, followed by metal ion reduction using a reducing agent such as sodium borohydride, was used to prepare the metal coated microspheres.

In the biotechnical arts, interest in metal-coated colloidal particles or substrates continues because, among other applications, these particles have the ability to enhance the right angle light scatter in flow cytometric forward versus side scatter histograms. It is expected that a thin coating of gold or silver on relatively large polystyrene particles (2.15 µm; 2150 nm) will show behavior similar to metal islands deposited on flat surfaces or microlithographically etched arrays and on roughened metal electrode surfaces. Each of these enhances light scattering with excitation in the visible light region into the characteristic plasmon or collective free electron oscillation bands of these metal structures.

In elastic scattering of light from small particles, the extinction is dependent on (1) the size of the particle relative to the wavelength of light being used; that is, the ratio $2\pi a/\lambda$; and (2) the refractive index of the irradiated material. Gustav Mie, in an effort to explain the colors of colloidal gold suspensions, was the first to obtain a general solution for the scattering of light by a homogeneous sphere [11–13]. The extinction spectrum of small particles has two components-absorption and scattering. The extinction, absorption and scattering efficiencies of small metallic spheres of copper, silver and gold have been calculated using Lorenz-Mie scattering theory [14–15]. The extinction band of colloidal gold spheres of 20 nm diameter in water has a maximum at 520 nm. Similar silver spheres show a maximum at 400 nm. Calculations have shown that at particular excitation wavelengths in the blue and red regions of the visible spectrum of gold and silver spheres of selected radii, scattering will dominate the extinction and absorption will be very small. For example, calculations involving silver spheres predict that for a small particle of about 5 nm radius, absorption dominates the extinction. For particles of about 50 and 500 nm radius, scattering dominates the extinction and absorption is of low intensity. In reality, since the deposited structures of gold and silver are not the isolated metal spheres of theory, the predicted wavelength dependencies of the efficiency factors will have to be modified to account for the various undefinable shapes of the individually deposited metallic bumps and for interactions between neighboring bumps. Both of these reality effects tend to broaden the extinction band and shift its maximum to longer wavelengths. In addition, the refractive index of actual gold and silver structures may not be the same as the bulk metal values that are used in the calculations.

Experiments with gold hydrosols show that elastic scattering is enhanced by excitation into the small particle plasmon resonances which were observed near 700 nm for small gold particles [16]. For microstructural gold or silver bumps on polystyrene microspheres, the bumps being about 50–200 nm in size and having about 50–200 nm spacing between themselves, elastic light scattering can be use to distinguish polystyrene particles, gold-coated polystyrene particles and silver-coated polystyrene particles from each other. The distinctions are made in forward versus side or orthogonal scatter histograms such as those obtained using a flow cytometer [17]. In fact, attempts have been made to use 40 nm diameter gold colloids with selected antibodies as light scattering probes in flow cytometry [18–20]. The results showed insufficient or less than optimal resolution of immunogold-labelled cells. The gold label increased side scatter signal amplitudes more than tenfold when 632.8 nm He-Ne excitation was used. Bohmer and King [18] proposed that gold particles larger than 40 nm might be even more useful in obtaining ever stronger light scatter signals. They conceded, however, that no such particle-antibody conjugates were available. As noted, the calculations of Messinger et al., Ref. 14, for gold spheres of 22 nm radius showed that absorption is still slightly greater than scattering at 632.8 nm.

The preparation in liquid medium of gold particles of uniform size, spherical shape and larger than 40 nm diameter is very difficult to accomplish unless gravitational effects on the heavy metal are absent. This was shown in the experiments of Frens [21] who used the citrate method to prepare six gold suspensions of different particle size ranging from 16 to 147 nm diameter. Gold particles greater than 40 nm in diameter showed an increased tendency to coagulate in the presence of electrolytes and to form polydispersed, non-spherical particles. In contrast to these metallic particles, buoyant polystyrene latex particles of low density, i.e. 1.05 g/cc versus 18.88 g/cc for gold and 10.5 g/cc for silver, can be obtained readily. These polystyrene particles can have a variety of surface functional groups, are available in various sizes and possess exceptional uniformity in their size and spherical shape. This uniformity in size and shape will be preserved when the particles are coated with a thin layer of gold or silver. For example, polystyrene particles of 2.15, 1.59, 1.01, 0.604 and 0.294 µm diameter can be coated with a thin layer of gold or silver, the thickness of the layer ranging from greater-than-zero to about 200 nm, depending on deposition conditions. Since the light scattering properties of colloidal particles depend only on the chemical composition and structure of the outermost layer of the particles, gold- or silver-coated polystyrene particles will have the same light scattering properties as finely dispersed pure gold or silver particles of the same size. The metal-coated polystyrene particles, however, are easier to keep suspended in solution because the density of such particles is considerably less that of pure metal particles of the same size. Gold or silver particles of, for example, 2.15 µM diameter would be very difficult to keep suspended. Lastly, there is a considerable cost saving because less precious metal is used in preparing metal-coated polystyrene particles of a given diameter than would be used in preparing pure precious metal particles of the same size.

Gold- or silver-coated particles 40 nm or smaller [1 nm=$10^{-9}$ meter (m)] in diameter cannot be seen using an ordinary light microscope. Visualization of submicron particles, those less than $10^{-6}$ m, requires the use of a special method whereby the particles are viewed using bright field or epi-polarization microscopy and electronically enhancing the contrast of the resulting image [22]. Larger particles, such as those in the 0.3–2.5 µm range, which have a thin gold or silver coating can be visualized easily in an ordinary light microscope. Larger gold-coated particles are blue-purple in color and larger silver-coated particles are dark green-grey or black.

By themselves, uniform polystyrene particles of diameter 0.3–2.5 µM show extensive light scattering because their large size gives $2\pi a/\lambda$ values greater than unity for light wavelengths in the visible region. The uniform size and shape of these particles makes them an ideal support for studying the effects of small gold or silver structures on various light scatter phenomena. Under favorable excitation wavelength conditions, at least one of the assorted metal coated polystyrene microspheres can be made to produce its maximum light scatter. The intensity of the light scatter will depend mainly on the refractive index properties of the small gold or silver structures present on the microspheres. These metallic structures also will give a degree of granularity or shape complexity to the entire particle which is similar to the granularity or shape complexity seen in biological cells [23]. The magnitude of this granularity or the scale of surface roughness (complexity) will mainly affect the amplitude of the side scatter. Forward scatter, also related to the size of the composite particle [24], is altered very little by size considerations alone when a thin metal coating, bump size of 200 nm or less, is applied to, for example, a 2150 nm (2.15 µm) diameter polystyrene particle. However, extinction properties of the metal coating must be taken into account when considering the amplitude of the forward scatter obtained using the metal coated polystyrene beads.

In the biotechnical arts, surface plasmon resonance has been used as a probe of the chemical environment near the surface of a thin film of metal evaporated onto a glass slide. Ivar Giaever reported using an island of indium or indium-gold as the substrate to adsorb a protein [25, 26]. A darkening of the slide was visually observed when an antigenic species present on the metallic surface was allowed to react with its corresponding antibody. This darkening phenomena was explained on the basis of the refractive index properties of the small indium particles [27]. At the wavelength of the incident light used in the experiment, 300 nm, Bohren and Huffman [27] showed that absorption, not scattering as proposed by Giaever, dominated the extinction and led to a a darkening of immunological slides when they were observed by transmitted light. Pharmacia Biosensor AB (Piscataway, N.J.) markets a similar surface plasmon sensor. The sensor consists of a thin gold film on the surface of the glass slide. The Pharmacia sensor is used with Pharmacia's BIAcore® instrument to monitor protein-protein and protein-ligand interactions by measuring binding and dissociation events as they occur [28].

One object of the present invention is to prepare uniform colloidal particles coated with a thin metallic layer, preferably colloidal particles which have a thin, uniform peripheral coating of metallic gold or silver. Another object of the invention is to use such metal-coated colloidal particles as shifting agents in various instrumental methods, including flow cytometry and Raman spectroscopy. A method is taught for preparing the particles of the invention and data is presented illustrating the utility of the invention.

SUMMARY OF THE INVENTION

The invention provides for colloidal particles comprising a metallic solid deposited on the peripheral surface of an aminodextran-coated, spherical, colloidal-sized core substrate. The core substrate used in producing the claimed particles can be of any colloidal dimensions and made of any substance provided that an aminodextran can be either adsorbed on or covalently bound to the peripheral surface of the substrate. For reasons of cost, availability, and uniform size and shape, polymeric substrates are preferred and polystyrene substrates are the optimum substrates. The aminodextran used in practicing the invention must be capable of reducing metal ions or complexes, particularly those of silver and gold, to the metallic state. The preferred aminodextrans have 5–20% diamine substitution as described herein and —$NH_2$ groups as terminal amine groups.

The invention also provides a method for preparing the desired colloidal particles. A colloidal core substrate is first coated with the selected aminodextran. The aminodextran-coated core substrate is then contacted with a solution containing metal ions or complexes which can be reduced to the metallic or metal(O) state by the aminodextran. The particles are then washed and stored in aqueous medium until use.

Lastly, the invention illustrates its utility by showing how the produced particles provide for a method of shifting light scatter in instrumental methods such as, for example, flow cytometry and Raman spectroscopy. In particular, the particles of the invention may be used to shift forward versus side scatter of flow cytometric histograms.

BRIEF DESCRIPTION OF THE DRAWINGS

FIGS. 1A and 1B are photographs of silver- and gold-coated microspheres, samples S3 and G6 respectively, taken at about 1160-fold magnification.

DETAILED DESCRIPTION OF THE INVENTION

Figure 2:
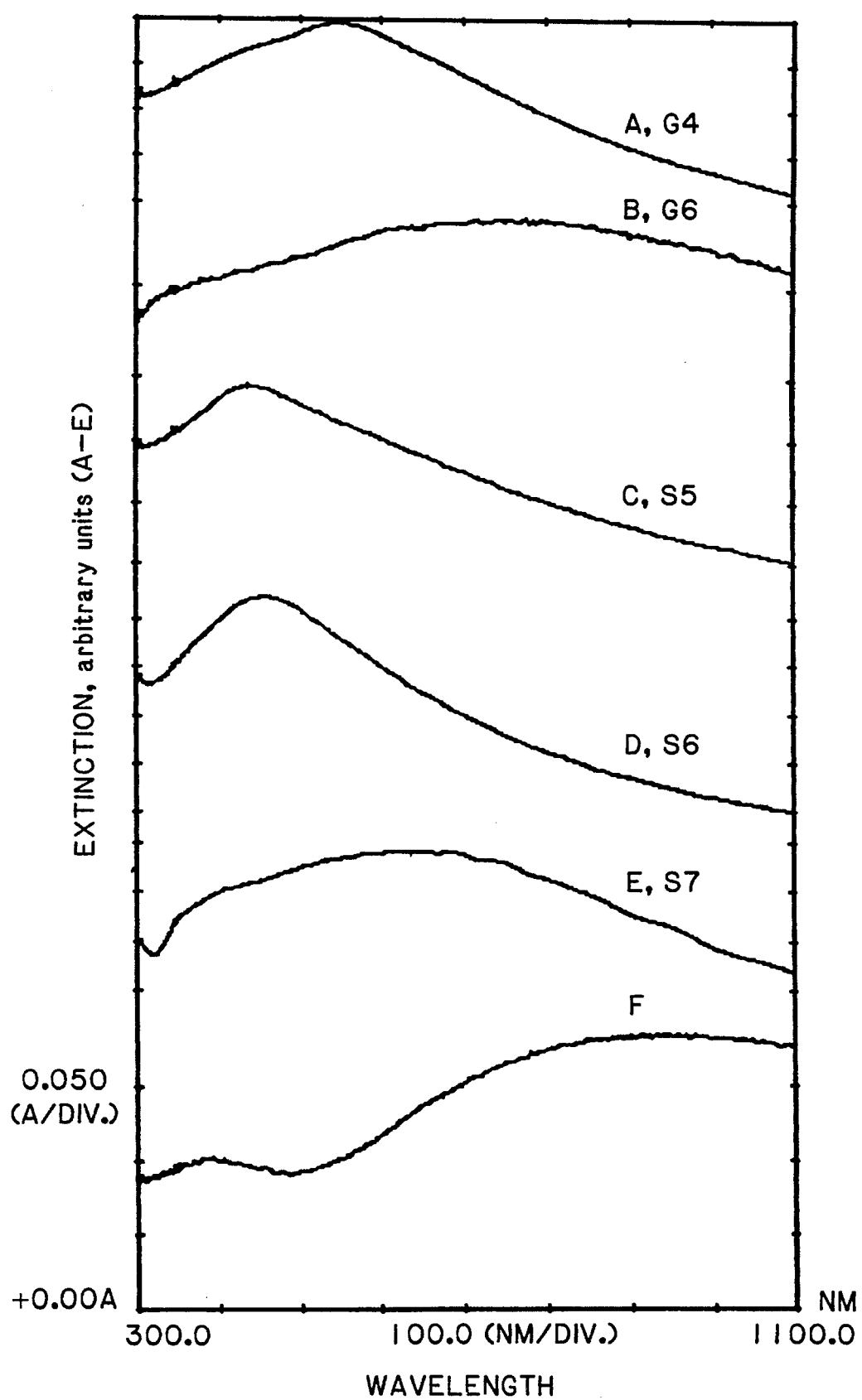
FIG. 2 is a composite extinction spectrum comparing various silver-and gold-coated microspheres (curves A–E) and uncoated polystyrene microspheres (curve F, no metal, no aminodextran) in the wavelength range of 300–1100 nm.

The claimed invention utilizes aminodextran compounds deposited on the surface of a colloidal size substrate to coordinate to and reduce metal salts or complexes to a metallic or metal(O) species which uniformly coats the surface of the aminodextran-coated colloidal substrate. Aminodextran compounds suitable for use in the claimed invention have been described in copending application Ser. No. 07/827,347, now U.S. Pat. No. 5,248,772 and Ser. No. 07/961,157, now abandoned. The teachings of these applications and U.S. Pat. No. 5,169,754 are incorporated herein by reference. Although different aminodextrans may be used in practicing the invention, aminodextrans having 5–20% diamine substitution are preferred and those with 12–16% substitution are most preferred. This percentage substitution is determined as the degree of diamine substitution in dextran after consideration of the theoretical value of substitution based on 100% periodate cleavage and 100% diamine substitution. The theoretical maximum substitution value is 1/2.5 or 40%. The aminodextran used in the examples given herein is called 5X-aminodextran or 5X-Amdex. 5X-Amdex was prepared as described herein and in copending application Ser. No. 07/961,157.

The method described herein for the preparation of colloidal, metal-coated particles may be used with any colloidal sized substrate which is either capable of adsorbing the selected aminodextran reducing agent onto its surface or covalently binding the aminodextran to its surface. The substrate may be porous or hollow, or solid and non-porous. In the biotechnical and immunological examples given herein, solid, non-porous polymeric substrates are preferred so that the aminodextran is adsorbed only onto the peripheral surface of the substrate.

Any polymeric material compatible with the selected aminodextran, the metal salt solution, and the other reagents used in the procedures may be used in practicing the invention. Such polymers include, for example, polystyrene (PS), polystyrene-divinylbenzene, polymethacrylate and polyphenylene oxide. Polystyrene and polystyrene latex substrates are preferred because of their availability as various sized microspheres or beads, inexpensiveness, compatibility with most biological systems and familiarity to those skilled in the art. The polymeric substrate may contain amine-reactive surface functional groups; for example, aldehydes, aldehyde/sulfate, carboxylic acids and esters, and tosyl groups.

Any metal salt or complex capable of being reduced to the metal(O) state by the selected aminodextran may be used in practicing the invention. In general, metal ions or complexes having a reduction potential of +0.7 volts or higher may be used according to the invention. [For examples, see Handbook of Physics and Chemistry, 64th Ed. (CRC Press, Boca Raton, Fla. (1983–1984), page D-164]. Gold and silver salts are preferred. Salts of Rh(III), Pd(II), Pt(II) and Ir(III) can also be used.

The general method of preparing the metal-coated, colloidal polymeric microspheres of the invention comprises coating a selected substrate with a selected aminodextran. The coating is done in aqueous solution. The aminodextran may be either only adsorbed onto the surface of the microspheres or it may be covalently bound to the microspheres through at least one of its amine groups provided that amine-reactive groups are present on the microspheres. The aminodextran-coated microspheres are separated from the coating solution and the aminodextran coating is crosslinked using a crosslinking agent such as glutaraldehyde. If the aminodextran has been covalently bound to the microspheres, crosslinking is optional. The aminodextran-coated microspheres are washed and contacted with a solution containing a selected metal salt. Amine groups on the aminodextran coordinate to the metal ions which are subsequently reduced to the metallic state by the aminodextran. The metal-coated microspheres are separated from the reaction solution, washed and used in subsequent procedures.

Unless specifically stated otherwise, the terms "metal-coated beads", "silver-coated beads" and "gold-coated beads", and their equivalents, mean a colloidal sized substrate which has a first coating of an aminodextran and a second "coating" of gold, silver or other metal. For example, in the specific examples given herein, the term "silver-coated beads" would stand for silver-coated, 5X-Amdex coated, polystyrene beads. Polystyrene beads in the examples which have only a 5X-Amdex coating are referred to as "5X-Amdex (only)" coated beads.

References

1. G.P. Goudonnet et al., Chem. Phys. Left. 92: 197 (1982).
2. J. W. S. Hearle et al., The Use Of The Scanning Electron Microscope (Pergammon Press, New York 1973).
3. J. Turkevich et al., Disc. Faraday Soc. 11:58 (1951).
4. O. Siiman et al., J. Phys. Chem 87: 1014 (1983).
5. N. Kawahashi et al.,m J. Mater. Chem. 1: 577 (1991)
6. E. Matijevic et al.,European Patent Application 0 462 388, filed May 6, 1991, published Dec. 27, 1991 and entitled "COATED PARTICLES, HOLLOW PARTICLES, AND PROCESS FOR MANUFACTURING THE SAME". Claims Priority of U.S. Ser. No. 07/549,930, filed Jun. 20, 1990, now U.S. Pat. No. 5,318,797.
7. N. Kawahashi et al., J. Colloid Interface Sci. 138: 534 (1990).
8. S. Margel, European Patent Application No. 177834, filed Jan. 15, 1986 and entitled "POLYALDEHYDE MICROSPHERES CONTAINING BOUND ELEMENTAL TRANSITION METAL AND OPTIONAL ANTIBODY OR OTHER PROTEIN USEFUL IN DIAGNOSES, CATALYSIS AND CELL SEPARATION OR LABELLING".
9. S. Efrima, Mod. Aspects Electrochem. 16:253 (1985).
10. K. Chang and T. E. Furtak, Eds., Surface Enhanced Raman Scattering (Plenum Press, N.Y. 1982).
11. G. Mie, Ann. Physik 25:377 (1908).
12. J. A. Stratton, Electromagnetic Theory (McGraw-Hill, New York 1941).
13. H. C. van de Hulst, Light Scattering By Small Particles (Wiley, New York 1957; Dover edition, New York 1981), pages 397–400 (Dover).
14. B. J. Messinger et al., Phys. Rev. (B) 24: 649 (1981).
15. D. S. Wang et al., Phys. Rev. (B) 24:1777 (1981).
16. C. G. Blatchford et al., Surface Sci. 120:435 (1982).
17. H. M. Shapiro, Practical Flow Cytometry, 2nd ed. (Alan R. Liss Inc., New York 1988).
18. R. M. Bohmer et al., Cytometry 5: 543 (1984).
19. R. Festin et al., J. Immunol. Meth. 101: 232 (1987).
20. T. H. Totterman and R. Festin in Colloidal Gold: Principles, Methods and Applications, Vol. 2, M. A. Hayat, Ed. (Academic Press, San Diego 1989).
21. G. Frens, Nature 241: 20 (1973).

22. U.S. Pat. No. 4,752,567, issued Jun. 21, 1988 to M. J. DeBrabander et al. and titled "METHOD OF VISUALIZING INDIVIDUAL SUBMICROSCOPIC METAL PARTICLES".

23. G. C. Salzmen et al., Acta Cytol. 19: 374 (1975).

24. P. F. Mullaney et al., Rev. Sci. Instrum. 40: 1029 (1969).

25. I. Giaever et al., J. Immunol. 110: 1424 (1973).

26. I. Giaever et al., Proc. Natl. Acad. Sci. USA 71: 453 (1974).

27. C. F. Bohren and D. F. Huffman, Adsorption and Scattering of Light by Small Particles (Wiley-Interscience, New York 1983).

28. M. Malmqvist, Nature 361: 186 (1993).

DESCRIPTION OF THE PREFERRED EMBODIMENTS

A. PREPARATION OF AMINODEXTRAN COATED MICROSPHERES

In general, polymeric microspheres (beads) in the size range 0.2–5.0 microns (μm) are used in practicing the invention. Aldehyde/sulfate polystyrene microspheres of the following diameters are preferred and were used in the examples which follow: 2.16 μm ±5.5%; 1.59 μm ±4.8%; 1.01 μm ±3.3%; 0.604 μm ±3.5% and 0.294 μm ±6.7%. These microspheres were obtained from IDC Corporation, Portland, Oreg.

Example 1. Preparation of 5X-Amdex

T-2M dextran (50 g, 0.308 mol, obtained from Sigma Chemical or Pharmacia) was added to a 1-quart or 1-liter glass blender bowl containing 300 ml of distilled water. The mixture was blended at maximum speed until all the dextran dissolved, typically 3–5 minutes. A solution of 26.75 g (0.125 mol) of $NaIO_4$ in 300 ml distilled water was added to the dextran solution over about a 10 minute period using vigorous magnetic stirring. After the periodate addition was completed, the reaction mixture was stirred at room temperature for an additional three hours. After the three hours, the 600 ml reaction volume had an initial specific conductivity of 9.7 mmho-cm$^{-1}$ and an initial pH of 2.5. The reaction mixture was diluted to two liters with distilled water and desalted using a hollow fiber cartridge (polysulfone, 3 ft$^3$ membrane surface area, 1 mm diameter fibers and 5,000 MW cut-off) vertically mounted with an input power pump (two pump heads, maximum flow rate of about 4.56 liters/minute with No. 18 Norprene® food grade tubing) delivering 15–20 psi which corresponds to 5–10 psi in the retenate line. The filtrate was collected at a rate of 50–100 ml/min. Washing was done using 15–18 liters of distilled water to obtain 600 ml of washed, oxidized dextran solution having a specific conductance of 10 mmho-cm$^{-1}$ and pH of 6.7.

The solution of oxidized dextran was cooled to about 8° C. using an ice bath and 23.2 ml (0.275 mol) of 1,3-diaminopropane was added over about 10 minutes to the oxidized dextran solution. The resulting reaction mixture was stirred and maintained at the ice bath temperature. The formation of the yellow Schiff's base was monitored every 10–15 minutes by measuring the 335 nm absorbance of an extracted sample. In a typical experiment, the measurements at 335 nm, using a 1 mm path length cell, were as shown in Table 1:

TABLE 1

| minutes | absorbance values |
|---------|-------------------|
| 0       | 0.100             |
| 5       | 2.063             |
| 15      | 2.975             |
| 30      | 3.692             |
| 45      | 3.901             |
| 60      | 4.103             |
| 74      | 3.784             |

After the absorbance had reached a plateau, 19.3 g (0.500 mol) of sodium borohydride in 19.3 ml of 1 mM aqueous potassium hydroxide was added to the reaction mixture over about 10 minutes at ambient temperature (room temperature, 15°–28° C.) and the resulting reaction mixture was stirred for two additional hours. After the stirring was completed, spectroscopic measurements at 335 nmn, using a 1 mm path length cell, gave an absorbance value of 0.067 units, which indicates that the Schiff's base compound had essentially disappeared. The reaction mixture, about 1000 ml volume, was then desalted using the hollow fiber cartridge. The initial specific conductance was 43 mmho-cm and the initial pH was 11.0. About 18–20 liters of distilled water was used as wash liquid to produce about 300 ml of 5X-Amdex solution having a specific conductance of 4–6 μmho-cm$^{-1}$ and a pH of 6.5–7.0. The 5X-Amdex solution was filtered through a 0.8 μm cellulose nitrate filter and freeze-dried over 48 hours in a model TDS-00030-A, Dure-Dry® microprocessor-controlled freeze-dryer (FTS Systems, Inc.) to produce 24 g (48% yield) of flaky, pale yellow crystals.

Elemental analysis: C=45.83%, H=7.00%, N=4.49%, O (by difference)=42.68%.

Calculated analysis for $C_{12}H_{22}O_{8.25}N$: C=46.15%, H=7.10%, N=4.48%, O=42.46%.

The empirical formula based on actual analysis is $C_{12}H_{22}O_{8.3}N$, which is very similar to the formula $C_{12}H_{22}O_{8.25}N$ based on 6 units of glucose per one unit of fully diamine-substituted sugar ring ($C_{12}H_{28}N_4O_3$). Therefore, the degree of diamine substitution in dextran was 1/7 (about 14%) in contrast to a theoretical value of 1/2.5 (about 40%) based on 100% periodate cleavage and diamine substitution. Repeat experiments using 100 and 300 grams dextran produced a product having the same 1/7 degree of substitution. In this application, a statement that an aminodextran has 5–20% amine groups mean that the degree of diamine substitution falls with the range of 1/20 to 1/5 respectively. These terms, 1/20 to 1/5 or 5% to 20%, may be used interchangeably.

Example 2. Coupling 5X-Amdex to 2.15 μm Microspheres.

2.5 g of solid 5X-Amdex were dissolved in about 50 ml of distilled water and mixed with 29.762 ml of 4.2% w/v solids polystyrene beads in a 250 conical bottom centrifuge tube. Sufficient distilled water was added to bring the total volume to 125 ml. The final concentrations of the beads and 5X-Amdex were 1% w/v solids and 2% w/v , respectively. The pH of the bead suspension was adjusted to 10.0 by the addition of 25 ml of 5M aqueous potassium hydroxide solution. The resulting mixture was then roller mixed overnight (about 8–16 hours).

Example 3. Crosslinking of 5X-Amdex on 2.15 μm Polystyrene Microspheres.

After the above overnight mixing was completed, 1.5 ml of 25% glutaraldehyde solution were added to the bead suspension to give a glutaraldehyde concentration of 3 mg/ml. The resulting suspension was roller mixed for one hour. After 5–10 minutes of mixing, the yellow color indicative of Schiff's base formation was noted. After the one hour of mixing, the Schiff's base mixture was transferred to a 500 beaker and was reduced by the addition of 588 mg of solid sodium borohydride. The borohydride containing reaction mixture was magnetically stirred for 30 minutes. Subsequently, the beads were separated and washed five times with distilled water by resuspension and centrifugation at about 2000 g using a Beckman J-6B centrifuge The wash supernatant liquids were discarded and the washed beads were resuspended in distilled water to yield a total volume of 125 ml of 1% w/v suspension of 5X-Amdex coated beads. 5X-Amdex coated beads of other sizes were similarly prepared with the exception that centrifugation of the 0.294 and 0.604 μm beads had to be carried out for 20 minutes at 5000 g on a Beckman Model L8-70M ultracentrifuge with a 50.2 Ti rotor using 30 ml hard polycarbonate tubes with appropriate caps.

B. PREPARATION AND EXTINCTION SPECTRA OF GOLD AND SILVER COATED POLYSTYRENE MICROSPHERES.

Example 4. Coating of 2.15 μm Polystyrene Latex Microspheres with Gold.

95 ml of chloroauric acid solution [118.6 mg $HAuCl_4 \cdot 3H_2O$ in 1 liter distilled water ($2.8 \times 10^{-4}$ M Au(III))] were stirred magnetically and heated to 90°–100° C. in a 250 ml flask. 10 ml of 1% solids 5X-Amdex coated 2.15 μm polystyrene beads were added to the hot gold(III) solution. The resulting mixture became very light pink in color after 5–10 minutes stirring at 90°–100° C. An additional 10 ml of the same bead suspension was added and the suspension immediately turned a dark red-purple color. The beads were washed three times with distilled water by centrifugation and resuspended in distilled water. The clear, colorless supernatant liquids, which indicate that all the gold(III) in solution reacted with the beads, were discarded. Microscopic examination of the beads at 1000× magnification showed a patchy red-purple coating of colloidal gold bumps on most of the polystyrene beads.

A parallel reaction was carried out as a control using polystyrene beads of the same size with no aminodextran coating. There was little or no color change after the first bead addition. About 10–15 seconds after the second bead addition, the reaction mixture became a dark purple suspension. Simultaneously, a ring of red-colored metallic gold was deposited on the inside surface the glass flask. After centrifugation, the supernatant of the control reaction was dark red-purple in color and the resuspended control residue was purple. A portion of the supernatant was filtered through a 0.2 μm filter. A dark red residue of colloidal gold was left on the filter. The filtrate was light yellow in color, indicating the presence of unreacted Au(III) in solution. Microscopic examination of the resuspended control residue showed a mixture of dark red aggregates of colloidal gold particles of various sizes and shapes and polystyrene particles having no surface deposits of colloidal gold. It was concluded that gold(O) formed at the surface of the uncoated polystyrene aldehyde/sulfate beads by reaction with the surface aldehyde groups. However, the gold(O) thus formed was neither stabilized nor retained in the form of colloidal gold bumps on the surface of the beads as were the colloidal gold bumps formed on the 5X-Amdex coated beads. Calculations indicate that there are $2.2 \times 10^{-3}$ mol aldehyde groups in 10 ml of 1% w/v solids bead suspension and that $0.286 \times 10^{-4}$ mol Au (III) ions were used in the reaction. According to the balanced redox equation for aldehyde/Au(III), they react in the ratio of 3:2, respectively. The concentration data given above indicate that despite the fact that there was a 51.3-fold excess of surface aldehyde groups at the first addition of polystyrene bead ($2.2 \times 10^{-3} \div 0.429 \times 10^{-4}$), no reaction of the beads with Au(III) was observed.

Example 5. Coating of 2.15 μm Polystyrene Latex Microspheres with Gold-Excess Au(III) Conditions.

0.120 g chloroauric acid (the standard amount) was dissolved in 95 ml of distilled water in a 250 ml flask and heated to 90°–100° C. with vigorous magnetic stirring. 10 ml of 1% w/v solids 5X-Amdex coated polystyrene beads were added to the hot, stirred solution. No color change was observed even though stirring and heating, normally carried out for 5 minutes under excess polystyrene bead conditions, was continued for one hour. Acid formed during the reaction (see equations below) was found to be best neutralized by the addition of 1 ml of 1.36M sodium citrate (the standard amount) after 1–5 minutes of stirring the hot bead-Au(III) mixture. Immediately after sodium citrate addition, the reaction mixture turned very dark wine-red in color. Mixing and heating were continued for 5 minutes after citrate addition. The reaction mixture was then cooled to room temperature and the particulate content of the flask was washed three times by centrifugation for 4 minutes at 3500 rpm in 50 ml tubes. The supernatant liquids from the washings were discarded and the final residue was resuspended in aqueous 0.01M sodium citrate. Large aggregates (mainly gold) were separated from the suspension by passing it successively through 30 μm, 12 μm and 5 μm pore rayon cloth. Microscopic examination showed that the final dark red-purple suspension comprised mainly single, purple-colored polystyrene particles.

In this example, even though Au(III) was present in large excess, its reaction with the glucopyranose sugar rings of the aminodextran compound did not go to completion. The following redox equation indicates that pH control is required.

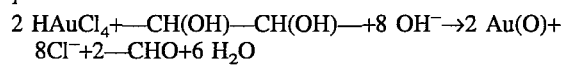

2 $HAuCl_4$+—CH(OH)—CH(OH)—+8 $OH^-$→2 Au(O)+ 8$Cl^-$+2—CHO+6 $H_2O$

When a strong base, for example, 0.5 ml of 5M KOH, was used in the above reaction sequence instead of sodium citrate, a dark purple reaction mixture resulted. However, microscopic examination of the particles showed that there were large aggregates of polystyrene beads and that Au(O) was only present, visibly, as particles between the polystyrene beads. When the 5X-Amdex coated beads were replaced in the reaction scheme by uncoated beads, the residue showed red colloidal gold particles of differing size and shape aggregated together with the uncoated beads.

As a result of these experiments, it was concluded that the kinetics of nucleation and growth of Au(O) particles had to be slowed down to obtain larger gold structures on the beads. This was achieved by lowering the reaction temperature to about 80° C., doubling the standard amount of chloroauric acid (to 0.240 g $HAuCl_4$ in 95 ml solution) and using one-half the standard amount of sodium citrate. Using these conditions and reaction times of 5 and 15 seconds after the addition of sodium citrate (achieved by quenching the reaction in a ice bath), polystyrene beads with surface gold bumps of irregular structure were produced. The suspended gold-coated polystyrene beads appeared brown in reflected light and blue in transmitted light.

Example 6. Coating 2.15 μm Polystyrene Latex Microspheres with Silver.

0.52 ml of 0.589M silver nitrate solution (0.306 mmol Ag(I)) was added to 95 ml of distilled water in a 250 ml flask. The solution was vigorously magnetically stirred and heated to 90°–100° C. 10 ml of 1% w/v 5X-Amdex coated polystyrene aldehyde/sulfate beads were added to the colorless hot silver solution and the mixture was stirred, with heating, for 1–5 minutes. The solution containing the mixture remained colorless. One (1) milliliter of 1.36M sodium citrate solution was added to the hot, stirred reaction mixture. Within one minute, the mixture turned yellow and then light reddish-brown. After about another minute, the mixture turned a dark red-brown. Finally, after 3–4 minutes total time, a dark grey to black suspension was produced. Three separate experiments were conducted which were quenched by cooling to room temperature after 1, 2 and 4 minutes reaction time. These experiments are hereafter designated as S5, S6 and S7, respectively. The solids were washed three times with distilled water by centrifugation as in Example 5. The clear, almost colorless supernatants were discarded and the final residues were resuspended in sufficient 0.01M aqueous sodium citrate to give a final volume of 15 ml for each trial (S5, S6 and S7). The contents of each trial run were passed successively through 30 μm and 12 μm pore rayon cloth and microscopically examined at 1000× (1 KX) magnification. The trials with 1 and 2 minute reaction times, S5 and S6, showed a light green, non-uniform coating of small silver bumps on the polystyrene beads. The trial with 4 minutes reaction time, S7, showed a uniform coating of large black silver bumps an almost all the polystyrene beads. FIG. 1 is a photograph of a drop of S7 suspension between a glass slide and a cover slip. The photograph was taken at 1160× (1.16 KX) magnification.

Example 7. Extinction of Specific of Ag- and Au-coated 2.15 μm Polystyrene Latex Microspheres.

The extinction spectra of the S5, S6, and S7 silver-coated beads were measured between 300 and 1100 nm on a Shimadzu Model 1604 UV-Vis spectrophotometer. In each case, the initial suspension (1% w/v solids) was diluted five-fold with distilled water. A sample of 5–10 drops of the diluted suspension placed on a clean glass microscope slide. The solution was evaporated to dryness to leave a uniform coating of beads on the glass slide. The coated area was masked off with black electrical tape in order to prevent light leaks during the spectrophotometric measurements. The spectra of S5, S6 and S7 are shown in FIG. 2. Spectra C (S5) and D (S6) show distinct broad bands centered at 435 and 458 nm, respectively. These peak maxima are red-shifted from their usual 400 nm position on the extinction band. This shift is typical of small colloidal silver particles of about 20 nm diameter. This shift indicates that the silver bumps immobilized on the 5X-Amdex coated polystyrene beads are substantially larger than 20 nm in diameter. Spectrum E (S7) shows a very broad extinction band centered at 638 nm. This is indicative of still larger colloidal silver bumps immobilized on the polystyrene beads.

In order to determine if the beads themselves present or cause any effects which must be taken into account, the extinction spectrum of uncoated polystyrene beads (no metal, no 5X-Amdex) was recorded. This is shown in FIG. 2, Spectrum F. The polystyrene beads generate a broad extinction band centered at about 1000 nm. This polystyrene band does not interfere with the extinction band recorded for colloidal, silver-coated polystyrene beads.

Figure 3A:
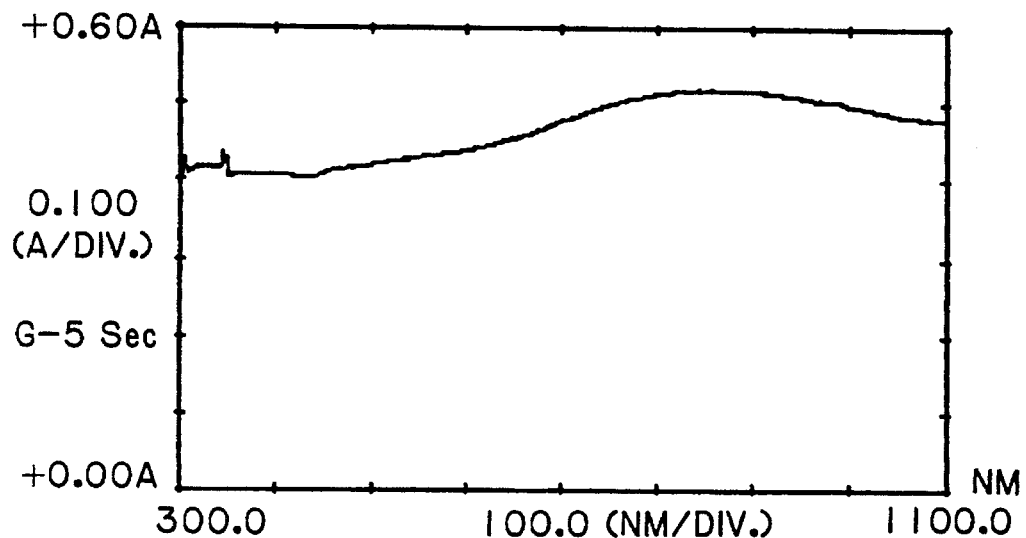
FIGS. 3A and 3B are the extinction spectra for gold-coated microsphere samples G-5 sec and G-15 sec, and illustrate the broad extinction bands shown when large gold bumps are deposited on microspheres.
Figure 3B:
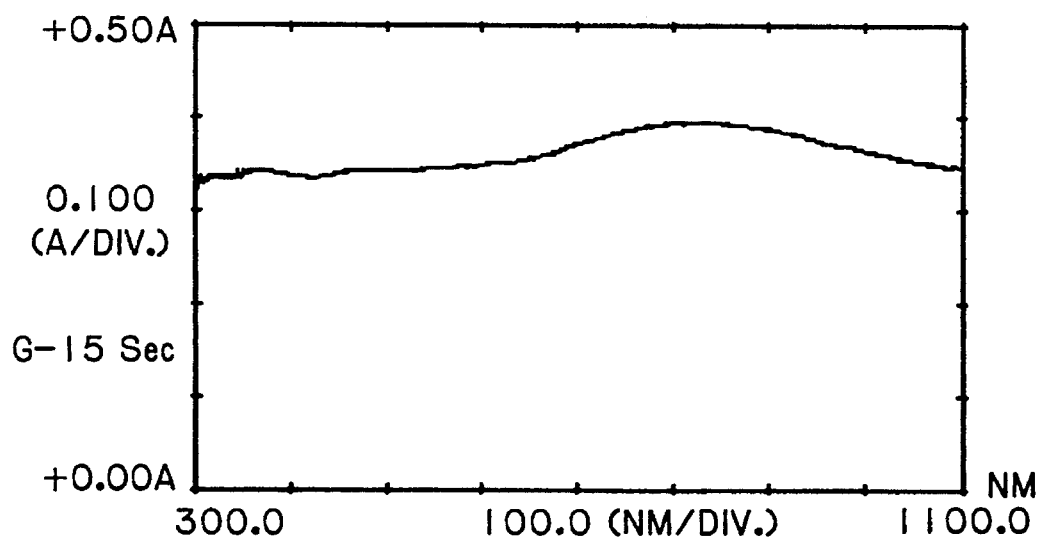

FIG. 2, Spectrum A (trial G4) was obtained using polystyrene beads which have small gold bumps deposited thereon. The coated beads show a broad extinction band centered at about 550 nm, which is slightly red-shifted from the 520 nm position normally assigned to 20 nm diameter colloidal gold particles or spheres. FIG. 2, Spectrum B (trial G6) was obtained using slightly larger gold bumps on 2.15 μm diameter polystyrene beads. These "slightly larger" gold bumps exhibit an extinction maximum near 750 nm. FIG. 3 illustrates "much larger" gold bumps on polystyrene beads. The extinction bands for the G-5 sec and G-15 sec beads are centered around 860 and 810 nm, respectively.

Example 8. Coating of Smaller Polystyrene Latex Microspheres with Silver.

The standard method for preparing silver-coated, 5X-Amdex polystyrene aldehyde/sulfate beads is described in Example 6. This method was also used to prepare similar particles using polystyrene aldehyde/sulfate beads of 0.294, 0.604, 0.101 and 1.59 μm diameter. The standard procedure was slightly modified in that the amounts of silver nitrate and sodium citrate were increased by factors of 7.310, 3.558, 2.132 and 1.348, respectively. These adjustments are necessary to compensate for the larger surface area for the same mass as the microsphere size gets smaller. All preparations yielded a suspension of black microspheres. Under 1000× microscopic examination, all individual polystyrene beads in each bead size were found to be completely coated with silver so as to give completely black particles. The small 0.294 and 0.604 μm beads also showed many aggregates of black beads.

Figure 4A:
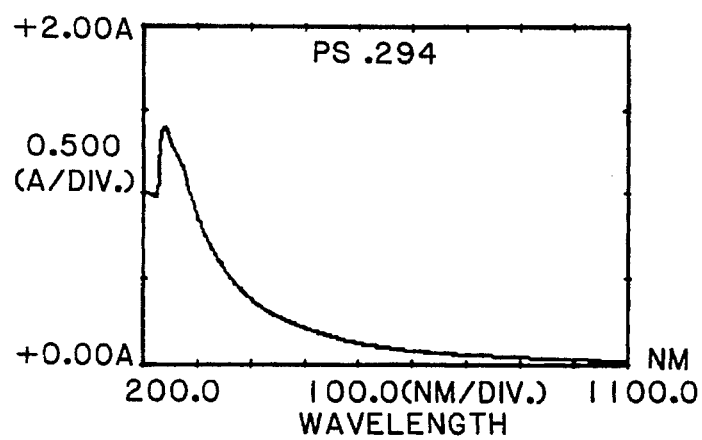
FIGS. 4A–4D illustrate the extinction spectra obtained using polystyrene aldehyde/sulfate microspheres (only) of different diameters.
Figure 4B:
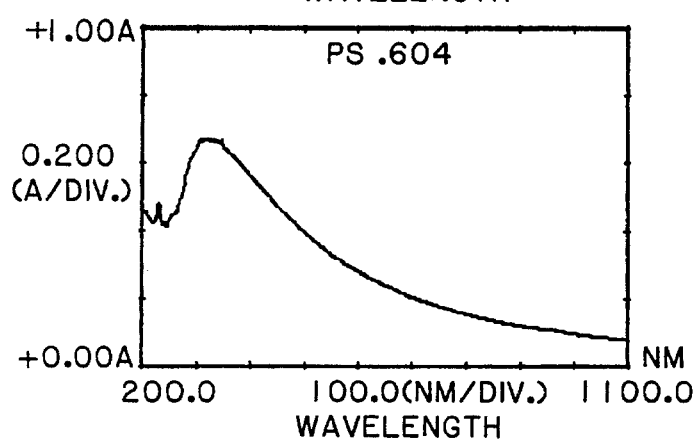
Figure 4C:
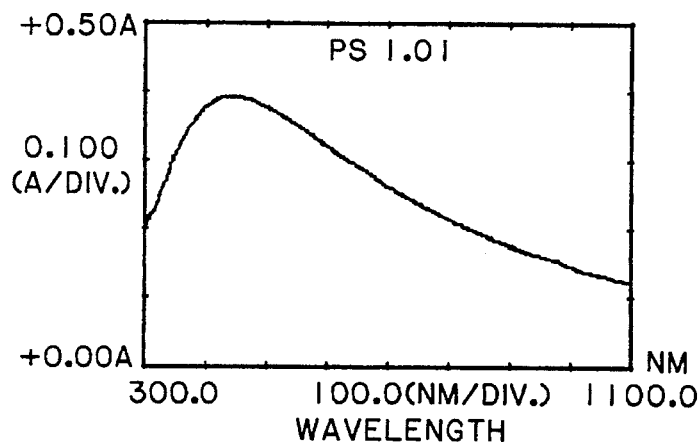
Figure 4D:
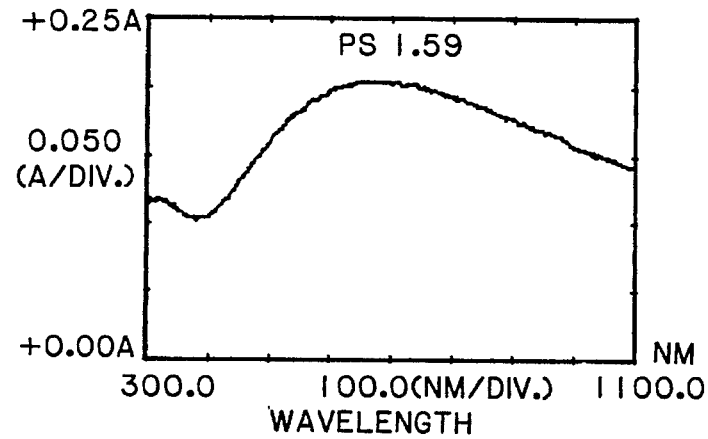
Figure 4E:
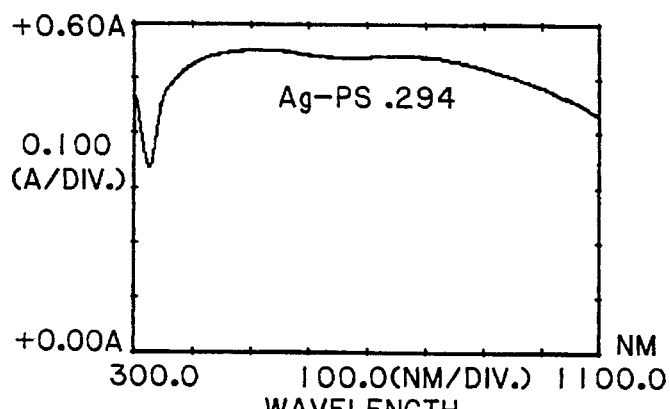
FIGS. 4E–4H illustrate the extinction spectra obtained using silver-coated colloidal polystyrene aldehyde/sulfate particles of different dimensions which were prepared according to the invention.
Figure 4F:
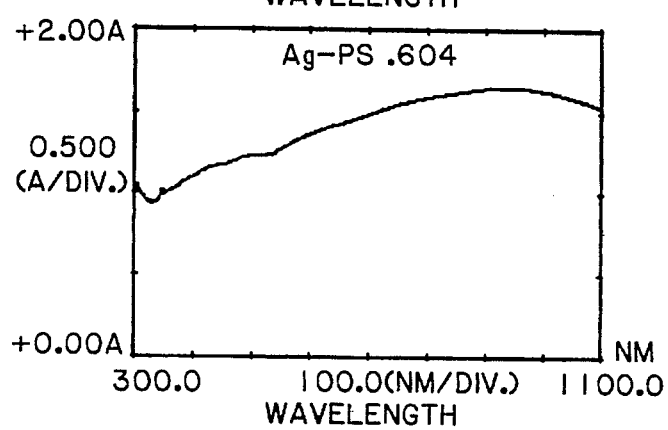
Figure 4G:
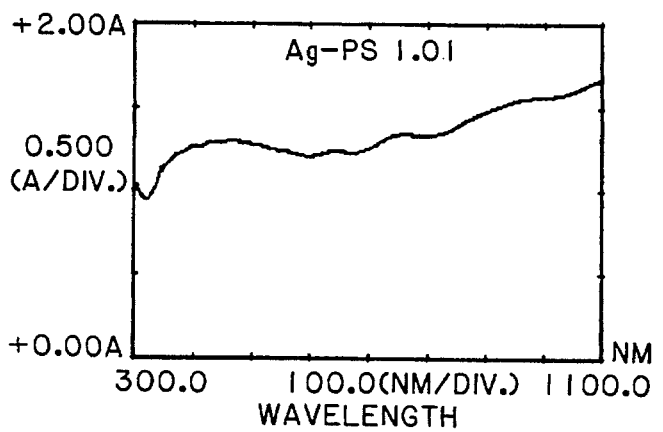
Figure 4H:
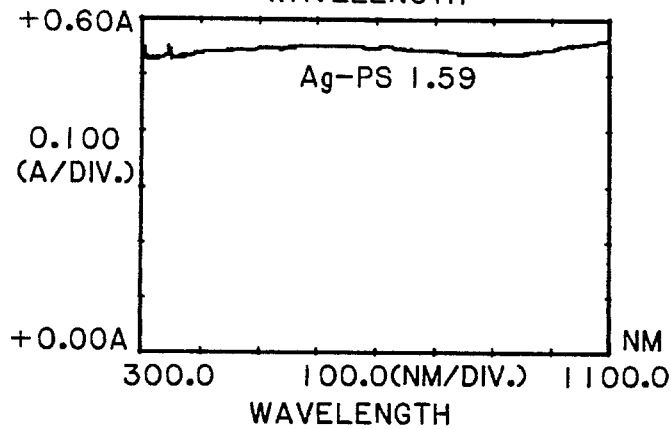

FIG. 4A–4D, represents the extinction spectra for 0.294, 0.604, 1.01 and 1.59 μm, uncoated polystyrene aldehyde/sulfate beads. The spectra were obtained using a 2000-fold dilution of the beads in distilled water. Extinction maxima for the particles occurred at 235, 320, 440 and 670 nm, respectively. FIG. 4E–4H, are the extinction-spectra of the corresponding silver-coated, aminodextran coated polystyrene beads. The spectra were obtained by evaporating the water from an aqueous suspension of the beads deposited on a glass slide. FIG. 4F, 0.604 μm beads, exhibits a maxima at 940 nm; and FIG. 4E, 0.294 μm beads, exhibits two maxima at 500 and 660 nm.

C. SCANNING ELECTRON MICROGRAPHS (SEM) OF GOLD- AND SILVER-COATED POLYSTYRENE MICROSPHERES.

Suspensions of gold- and silver-coated, 5X-Amdex polystyrene beads were prepared to have about 0.1% w/v solids. A drop of either the silver or gold 0.1% w/v suspension was applied to a metal stub that had been cleaned in absolute ethanol and dried in a vacuum desiccator. After depositing the drop, part of it was withdrawn using a Pasteur pipette and the residue on the stub was evaporated to dryness in a vacuum desiccator. In some experiments, a strip of conducting carbon tape was applied to the stub before the sample droplet was deposited. This allowed the use of higher SEM magnifications without charging the sample and losing resolution. FIGS. 5 and 6 represent typical SEM results obtained using silver- and gold-coated beads, respectively.

Figure 5A:
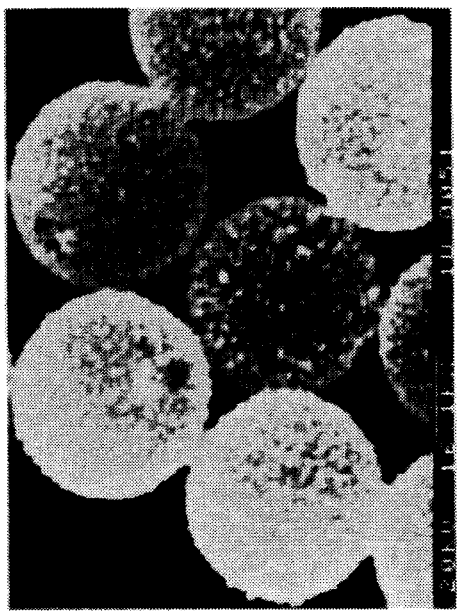
FIGS. 5A and 5B are two different SEM micrographs of the silver-coated microspheres of samples S1 taken at 32.1 KX and 6.42 KX magnification, respectively.
Figure 5C:
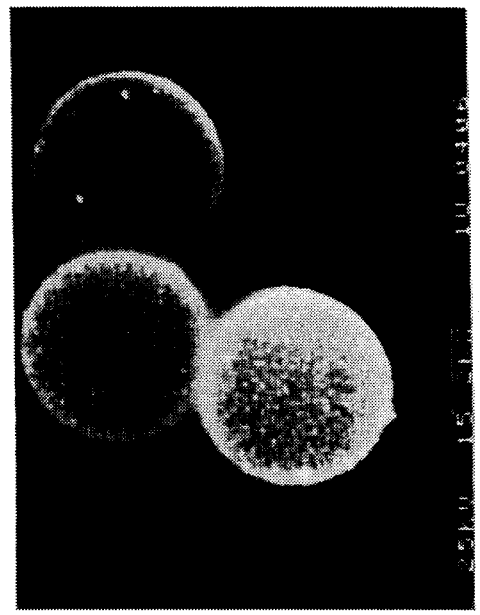
FIGS. 5C and 5D are two different SEM micrographs of the silver-coated microspheres of sample S3 taken at 16.1 KX and 15.2 KX magnification, respectively.
Figure 5B:
Figure 5D:
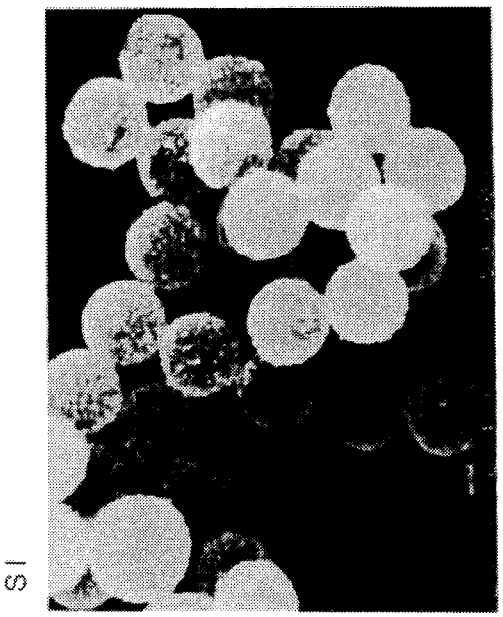

The SEM results shown in FIGS. 5A and 5B were obtained using trial S1 and those shown in FIGS. 5C and 5D were obtained using trial S3. These SEM results show that all beads were uniformly coated with colloidal silver structures 50–200 nm wide. Some of the silver structures, or bumps, on the polystyrene surfaces are interconnected by silver bridges. Several additional trial preparations were made in which the relative proportions of reactants, that is, silver nitrate and sodium citrate, were varied. These variations resulted in coated particles in which there were slight changes in the scale of roughness of the silver bump. For example, the use of more silver nitrate in trials S1 (1.55 ml of 0.589M AgNO₃) and S4 (1 ml of 0.589M AgNO₃) resulted in larger silver bumps. SEM photographs of trial S5, which has a one minute reaction time after sodium citrate addition, showed no resolvable silver structure. SEM photographs of trial S6, two minutes reaction time, showed barely resolvable, finely divided silver structures about 50 nm in width.

Figure 6C:
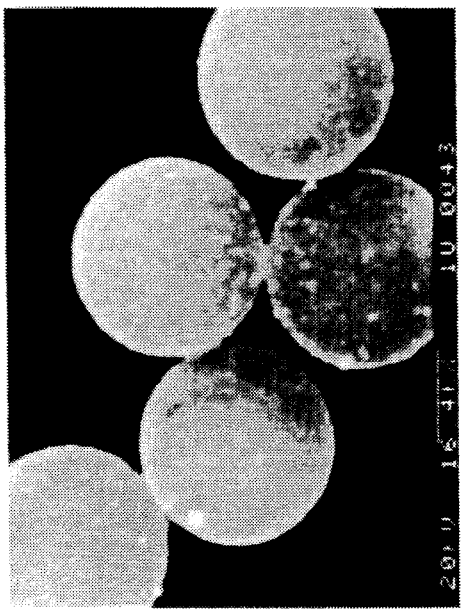
FIGS. 6A and 6C are SEM micrographs of the gold-coated microspheres of sample G6 taken at 15.0 KX and 16.4 KX magnification, respectively.
Figure 6D:
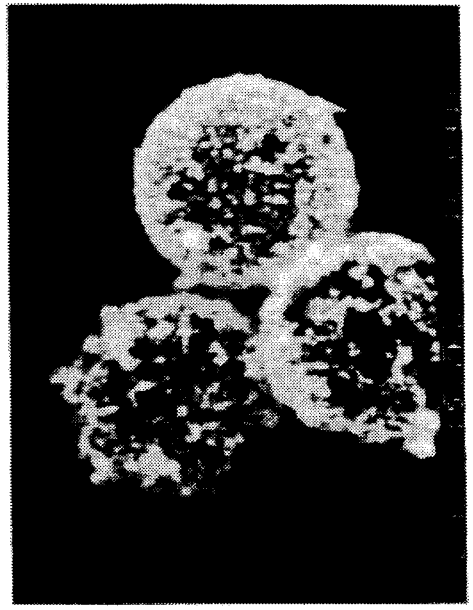
FIG. 6D is a SEM micrograph of the gold-coated microspheres of sample G-15 sec taken at 15.7 KX magnification.
Figure 6A:
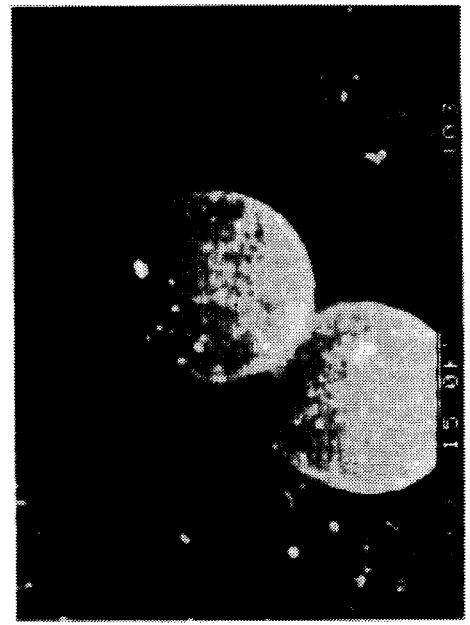
Figure 6B:
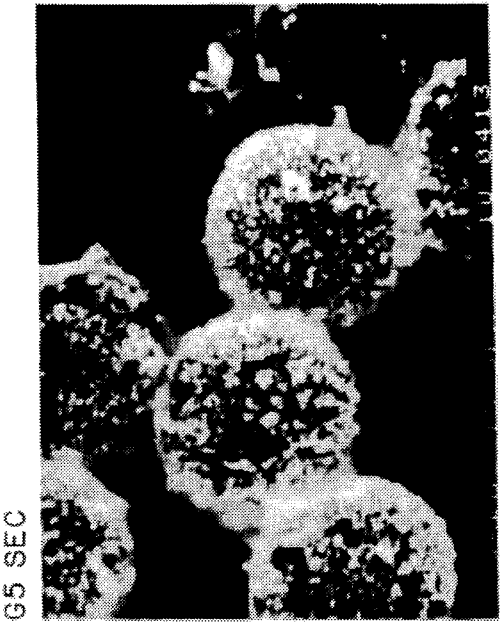
FIG. 6B is a SEM micrograph of the gold-coated microspheres of sample G-5 sec taken at 15.9 KX magnification.
Figure 7C:
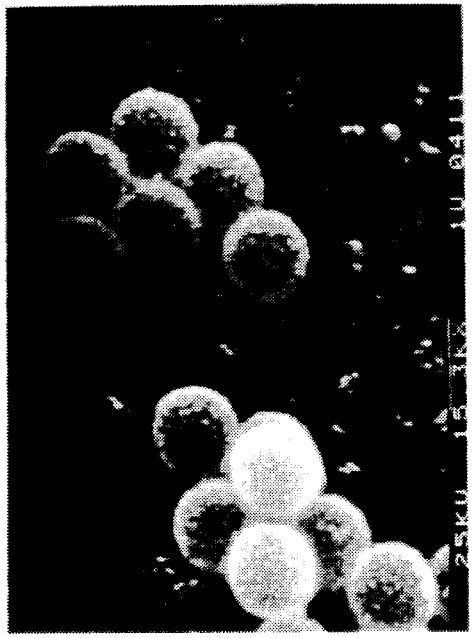
FIGS. 7A–7D are SEM micrographs (15.8, 30.6, 15.3, and 30.6 KX magnification, respectively) of silver-coated microspheres in which the polymeric cores have a diameter of 1.59, 0.604, 1.01 and 0.294 microns, respectively. The length of the white line at bottom, left of center, in each photo corresponds to one micron.
Figure 7D:
Figure 7A:
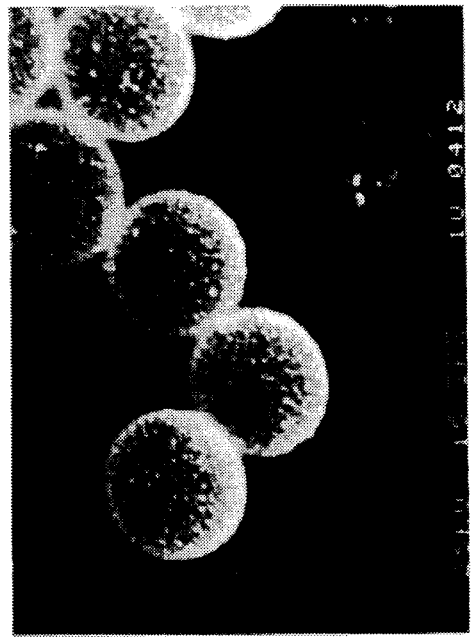
Figure 7B:

FIGS. 6A–6D are SEM photographs obtained using gold-coated beads. FIGS. 6A and 6C were obtained using trial G6. FIGS. 6B and 6D were obtained using trials G-5 sec and G-15 sec, respectively. The gold-coated beads exhibit many bare patches of polystyrene surface which has no apparent gold structures. Trials G-4 and G-6 show mostly much smaller structures below 50 nm diameter whereas trials G-5 sec and G-15 sec show structures in the same size range as the silver-coated beads; that is, structures 50–200 nm diameter. The SEM photographs of silver on smaller polystyrene beads of 1.59, 1.01, 0.604, and 0.294 μm diameter (FIG. 7) show colloidal size bumps similar in size to silver on 2.15 μm diameter beads, and does not tend to form a complete layer of silver metal on the beads.

D. LIGHT SCATTERING FROM GOLD- AND SILVER-COATED POLYSTYRENE PARTICLES

Forward versus side scatter histograms of assorted particles, both coated and uncoated, were obtained using a Coulter EPICS® Elite flow cytometer. Prior to running each set of samples, DNA-Check fluorescent microspheres were used to check instrument performance [coefficient of variation (CV) for position in forward (FS) versus side scatter (SS) histogram should be $\leq 2\%$. The linear scale was used in all FS vs. SS histograms. A mixture of 5X-Amdex (only), silver-coated and gold-coated polystyrene beads were first aspirated in each run to establish a suitable position of control beads and shifted, silver and gold-coated beads in the FS vs. SS histogram. Standard PMT voltages and amplifier gains were 900 V and 75, respectively, for FS and 450V and 15 for SS at $\lambda_0$=488.0 nm; and 790 V and 50 for FS and 405 V and 15 for SS at $\lambda_0$=632.8 nm. Run time for all samples was 2.0 min. The PMT voltages of SS detectors were varied between 455 and 300 V to verify that the selected voltage was in a linear voltage versus side scatter intensity region so that shifted SS intensities could be placed on an accurate relative intensity scale.

Figure 8A:
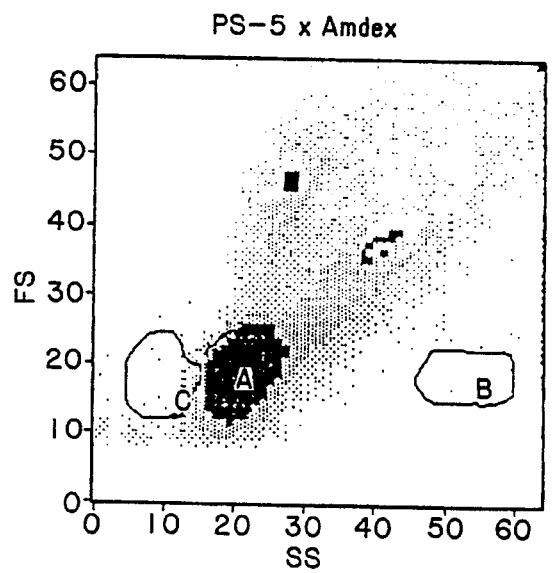
FIGS. 8A–8F illustrate forward versus side scatter in histograms of 5X-Amdex (only) coated polystyrene microspheres (8A), two different gold-coated microsphere samples (8B and 8C) and three different silver-coated microsphere samples (8D–8F) when a 488.0 nm $Ar^+$ laser line is used for excitation.
Figure 8B:
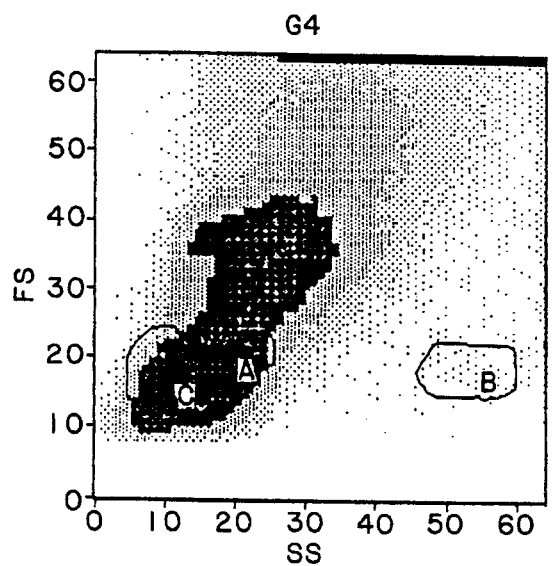
Figure 8C:
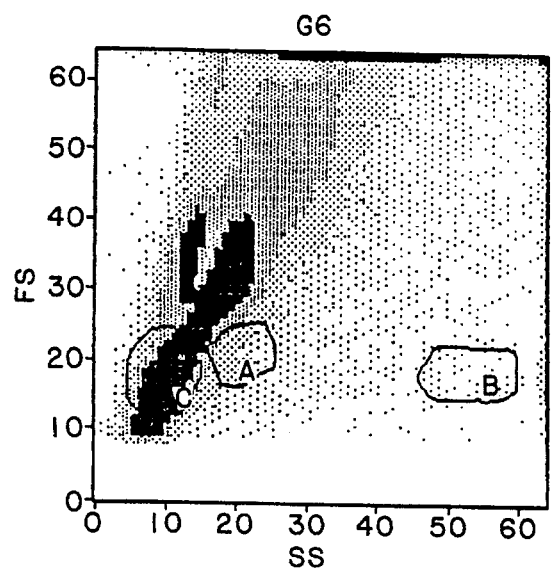
Figure 8D:
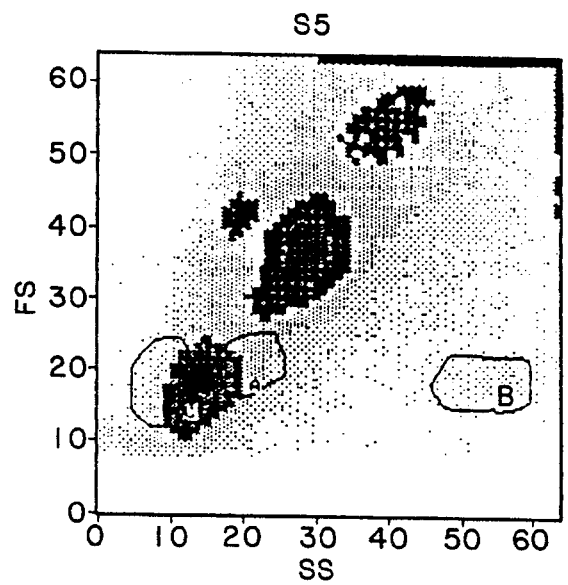
Figure 8E:
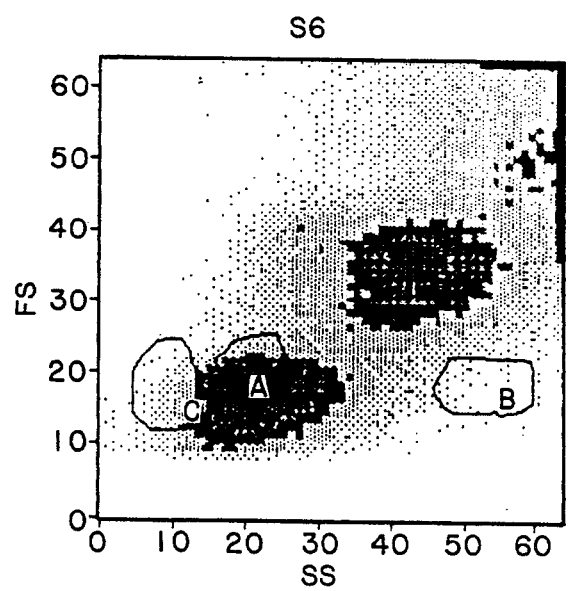
Figure 8F:
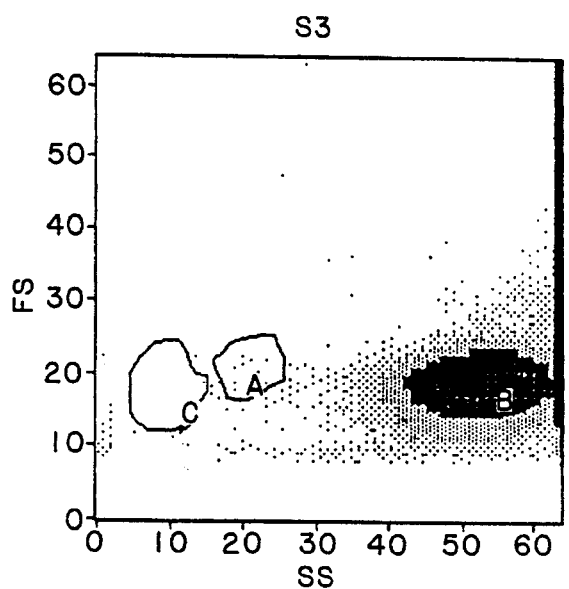

The histograms of 5X-Amdex (only), silver-coated and gold-coated polystyrene aldehyde/sulfate beads were obtained using several laser excitation lines. For an Ar+ laser, the lines were 457.9 and 488.0 nm. For a He-NE laser, the lines were 544 and 632.8 nm. Samples were diluted 100:1 with 0.01M sodium citrate solution (100 parts citrate to 1 part sample) before cytometry. Differences in scattered light intensity between samples with small or large structures of silver or gold on the polystyrene beads and excited with either 488.0 nm (shown in FIG. 8) or 632.8 nm (shown in FIGS. 9 and 10) laser lines correlated with theoretical predictions. Using excitation in the 458–676 nm range, beads with large silver bumps in the 50–200 nm diameter range showed a slight decrease in forward scatter when compared with Amdex (only) coated polystyrene beads (reference). However, the silver-coated beads with 50–200 nm bumps showed 2–3 times greater side scatter intensity relative to the reference (FIG. 8F, trial S3). The histograms of trials S3 and S7 showed no beads populating the histogram region normally occupied by 5X-Amdex (only) coated polystyrene beads. Trials S2 and S4, in which the silver structures (bumps) are smaller than S3, showed about a two-fold increase in side scatter intensity. Trials S5 and S6, in which the silver structures are so very small that they were not discernible under microscopic examination at 1000×, showed a decrease in side scatter ranging from two-thirds the intensity of the reference 5X-Amdex (only) coated beads (FIG. 8D, trial S5) to about equal to reference bead side scatter (FIG. 8E, trial S6).

Mie theory predicts that for small silver spheres of 5 nm radius, both extinction (absorption) and scattering at 488.0 nm are small. The observed small changes in histogram position for polystyrene beads coated with small silver bumps is in agreement with theory. For larger silver spheres of about 100 nm diameter, Mie theory predicts a large extinction (scattering) and a small absorption at 488.0 nm. The histograms for polystyrene beads which have large silver bumps show increased side scatter intensity and a decreased or equivalent forward scatter intensity. These histogram results agree with theory.

Figure 12A:
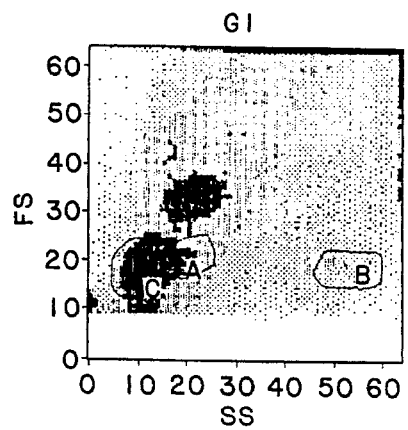
FIGS. 12A–12F correspond to FIGS. 10A–10F, respectively, but were obtained using a 457.9 nm $Ar^+$ laser line for excitation.
Figure 12B:
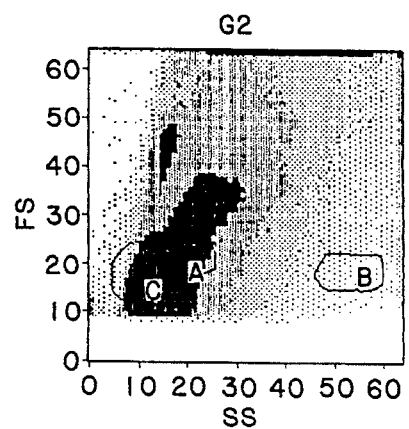
Figure 12C:
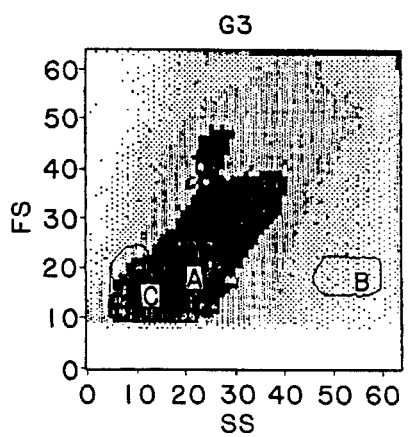
Figure 12D:
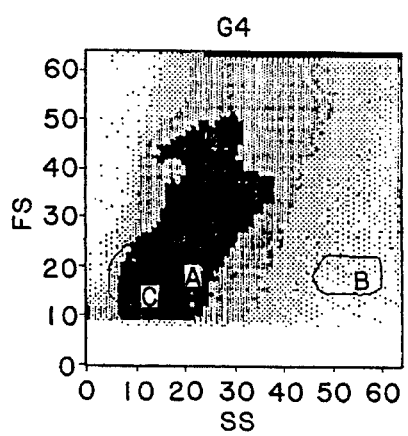
Figure 12E:
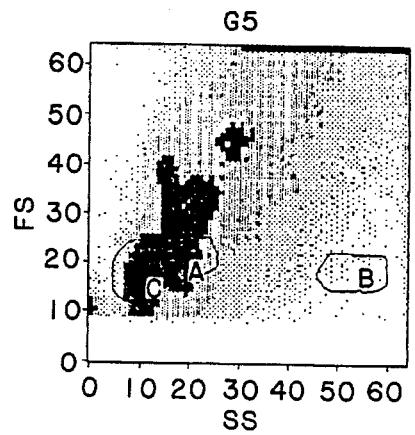
Figure 12F:
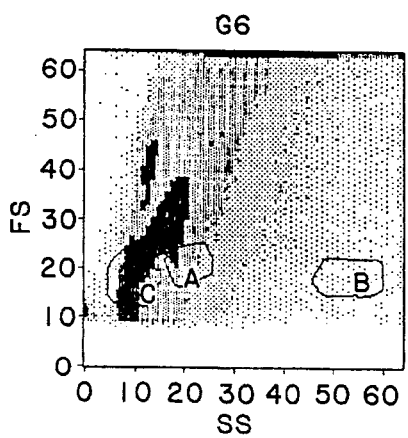
Figure 12G:
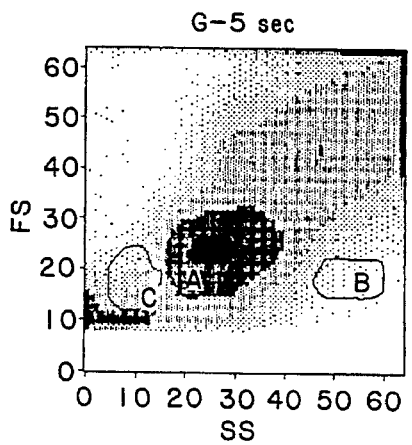
FIGS. 12G and 12H correspond to FIGS. 10G and 10H, respectively, but were obtained with a 488.0 nm $Ar^+$ laser line for excitation.
Figure 12H:
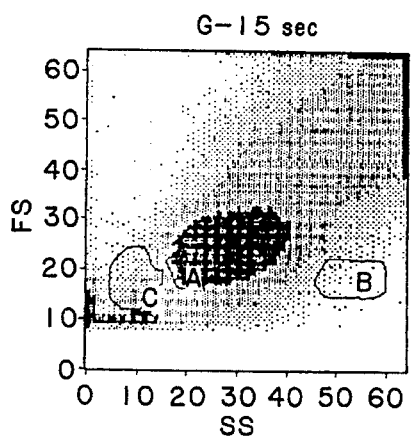

The results using gold-coated polystyrene beads were different. Most beads with small gold bumps showed a small decrease in forward scatter and a two-fold decrease in side scatter intensity relative to the reference uncoated polystyrene beads when 488.0 nm A+excitation was used. (See FIG. 8B, trial G4, and FIG. 8C, trial G6.) Histograms of many of the gold-coating trials also showed a substantial population of unshifted beads. This indicates the presence of a significant number of polystyrene beads that are either uncoated or only sparsely coated with gold. There are too few gold bumps on the surface to cause shifting. The histogram results obtained using 488.0 nm excitation also indicate that large gold bumps could be formed on a bead surface and produce very little shift in either forward scatter or side scatter relative to reference 5X-Amdex (only) coated polystyrene beads. [See FIGS. 12G and 12H, trials G-5 sec and G-15 sec, respectively, using 488.0 nm excitation.] Mie theory scattering calculations for small gold particle of about 22 nm radius predicts that extinction (adsorption) will be of medium magnitude at 488.0 nm and scattering intensity will be small. The results shown in FIGS. 8B and 8C for polystyrene beads coated with small gold bumps are in agreement with theory and show a decrease due to absorption in side scatter and forward scatter intensity. For large gold spheres of 100 nm radius, Mie theory predicts that both absorption and scattering contributions to the extinction at 488.0 nm will be low. The results shown in FIGS. 12G and 12H are in agreement, showing very small shifts in forward scatter and side scatter for beads coated with large gold bumps.

When histograms were obtained using 632.8 nm He-Ne excitation, large silver bumps on polystyrene beads showed a large shift to higher side scatter intensity (FIG. 9B–9E and 9H, trials S1–S4 and S7). These results are similar to those obtained using a 488.0 nm A+excitation line. However, unlike the results at 488.0 nm, forward scatter in the 632.8 nm histogram was reduced by a factor of two due to an increase in extinction in the red region (FIG. 2, Spectrum E, trial S7). Using 632.8 nm excitation, large gold bumps on polystyrene beads also produced a large shift in side scatter intensity and an even larger decrease in forward scatter (FIG. 10G, G-5 sec—633 and 10H, G-15 sec—633) due to an increased extinction in the red (see FIG. 3, A & B). However, small bumps of either silver (FIG. 9F and 9G, trials S5 and S6) or gold (FIG. 10A–10F, trials G1 to G6) on polystyrene beads showed either no shift in forward scatter intensity or a small shift to lower intensity, and no shift in side scatter intensity. Mie theory calculations for either silver or gold spheres of 100 nm radius predicts that extinction (scattering) is large at 632.8 nm while adsorption is very low. Theory and the experimental results are in agreement. For both large silver and large gold bumps on polystyrene beads, there is an observed drop in forward scatter intensity due to a large side scatter and a large side scatter shift. There is also agreement with the observed extinction maxima in the red region for both types of coated beads. With regard to 5 nm silver spheres and 22 nm gold spheres, Mie theory predicts that both absorption and scattering contributions to extinction will be very low when 632.8 nm excitation is used. This agrees well with the observed light scattering properties of small silver and gold bumps on polystyrene beads.

Figure 9A:
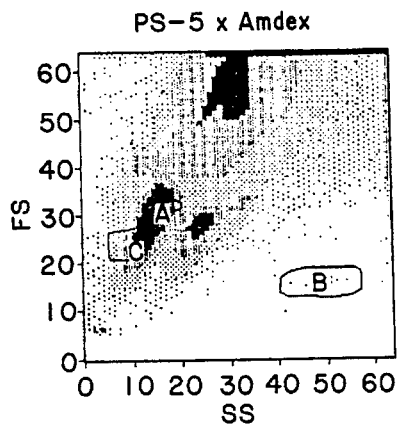
FIGS. 9A–9H illustrate forward versus side scatter in histograms of 5X-Amdex (only) coated polystyrene microspheres (9A) and seven different silver-coated microsphere samples (9B–9H) using a 632.8 nm He-Ne laser line for excitation.
Figure 9B:
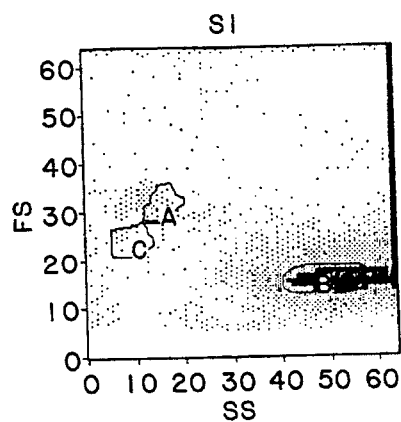
Figure 9C:
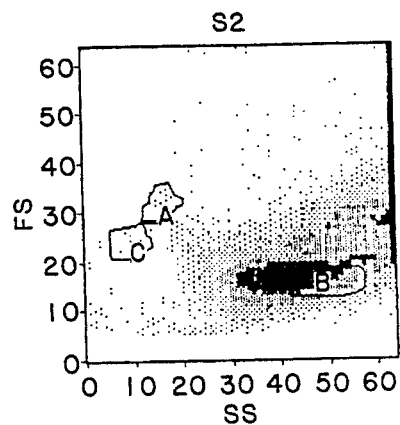
Figure 9D:
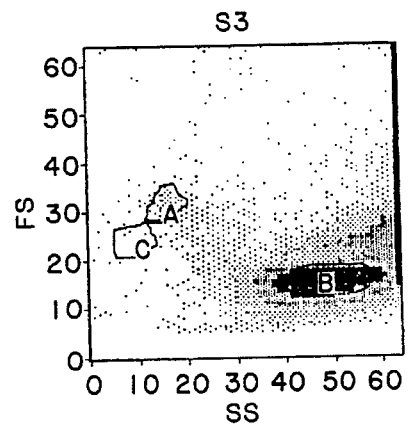
Figure 9E:
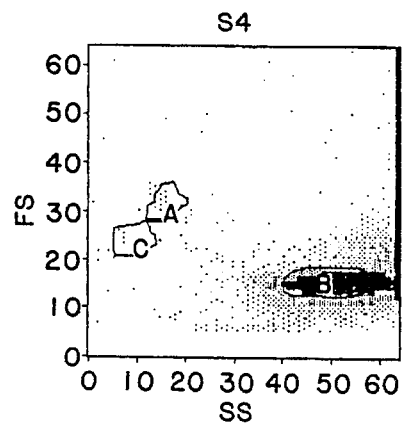
Figure 9F:
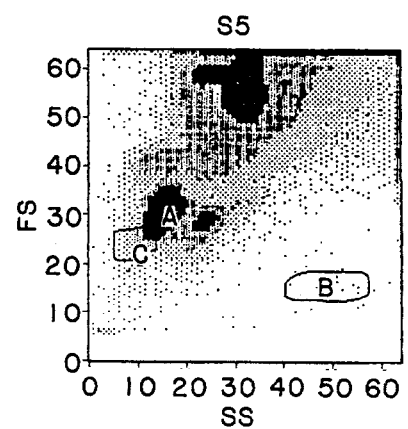
Figure 9G:
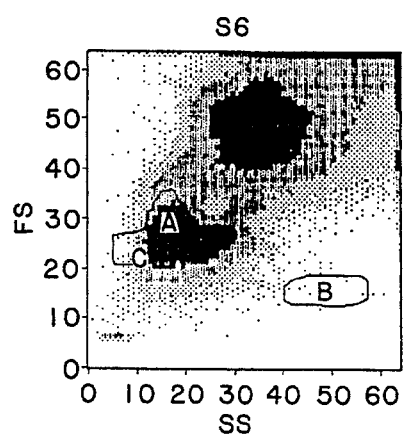
Figure 9H:
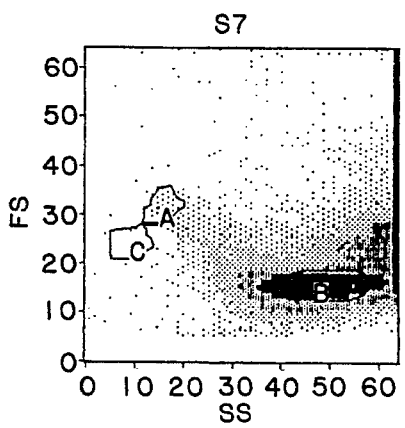
Figure 10A:
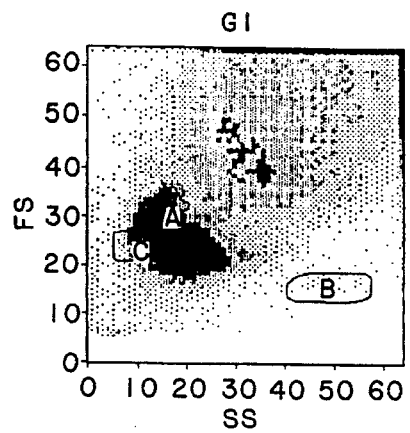
FIGS. 10A–10H illustrate forward versus side scatter in histograms of gold-coated microsphere samples, G1 to G6, G-5 sec and G-15 sec when the exciting radiation is a 632.8 nm [shown as 633] He-Ne laser line.
Figure 10B:
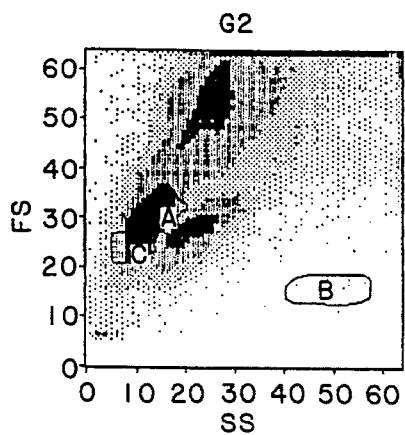
Figure 10C:
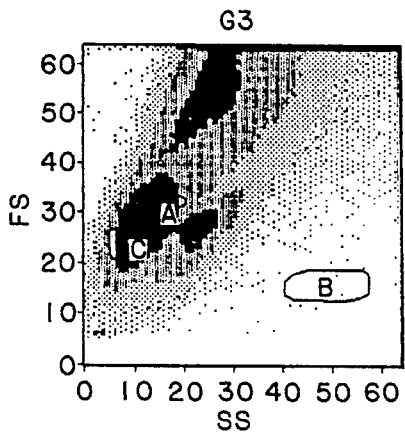
Figure 10D:
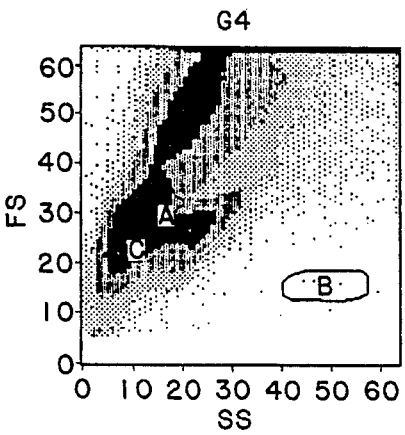
Figure 10E:
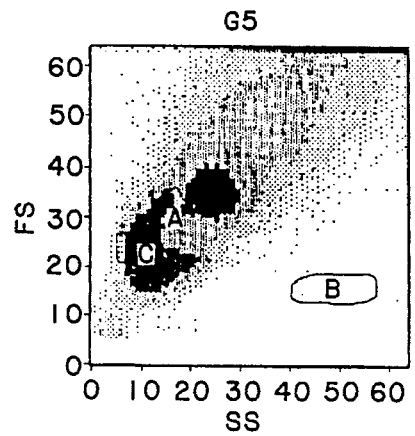
Figure 10F:
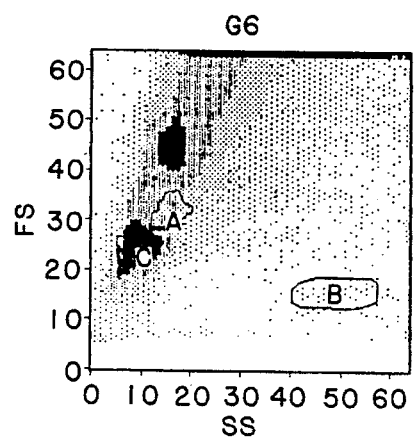
Figure 10G:
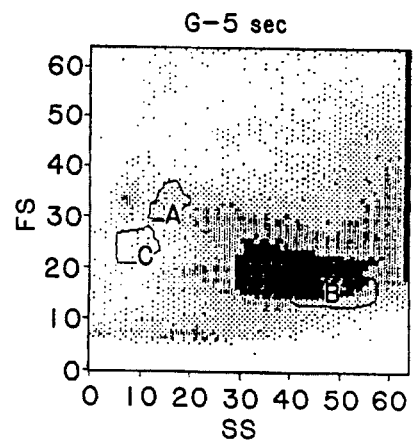
Figure 10H:
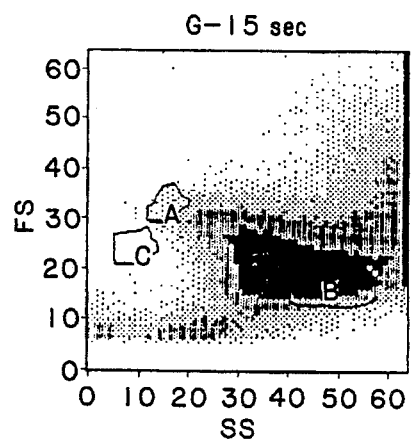
Figure 11A:
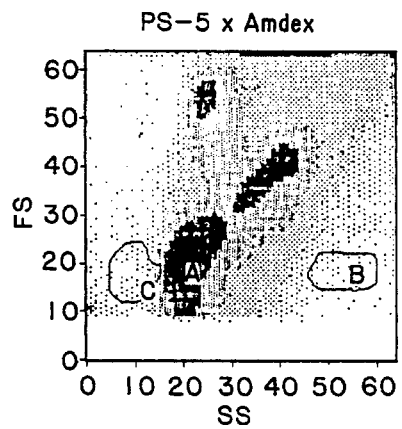
FIGS. 11A–11H correspond to FIGS. 9A–9H, respectively, but were obtained using a 457.9 nm $Ar^+$ laser line for excitation.
Figure 11B:
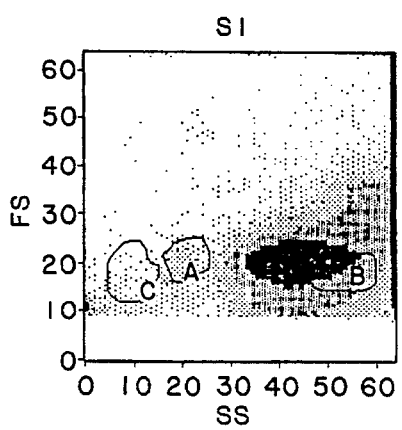
Figure 11C:
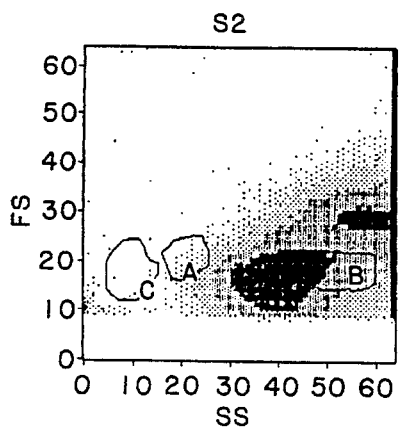
Figure 11D:
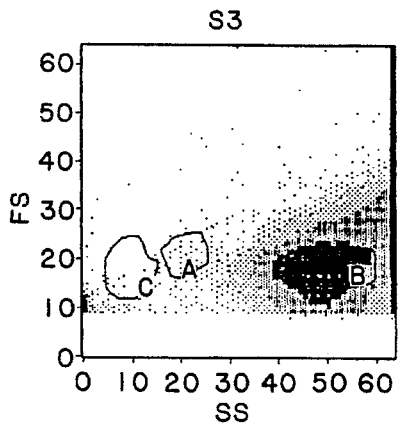
Figure 11E:
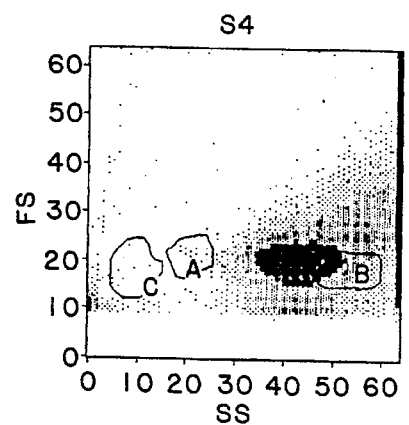
Figure 11F:
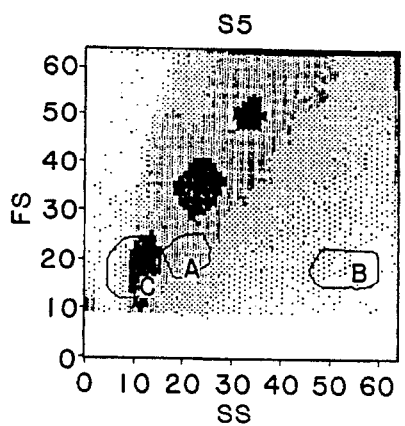
Figure 11G:
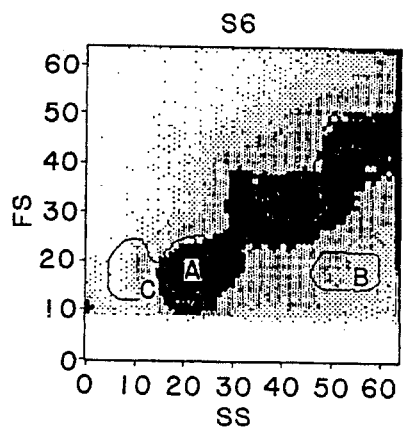
Figure 11H:
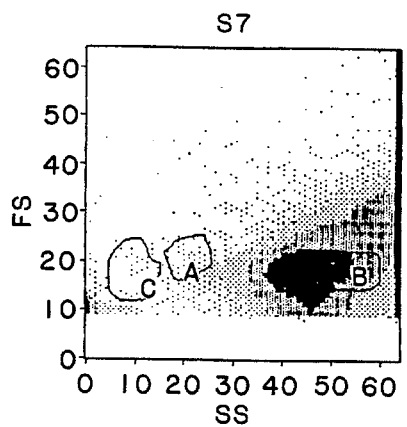
Figure 13A:
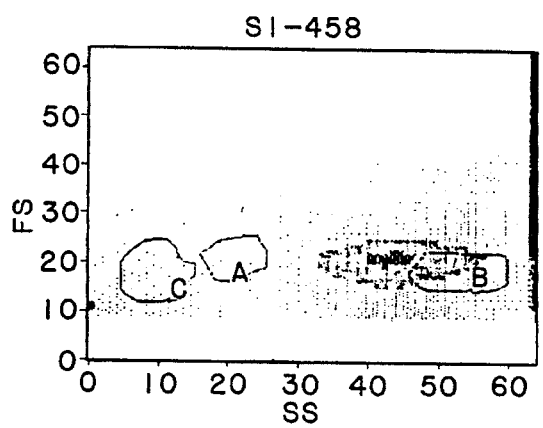
FIGS. 13A–13D illustrate forward versus side scatter in histograms of silver-coated microsphere sample S1 taken at various wavelengths.
Figure 13B:
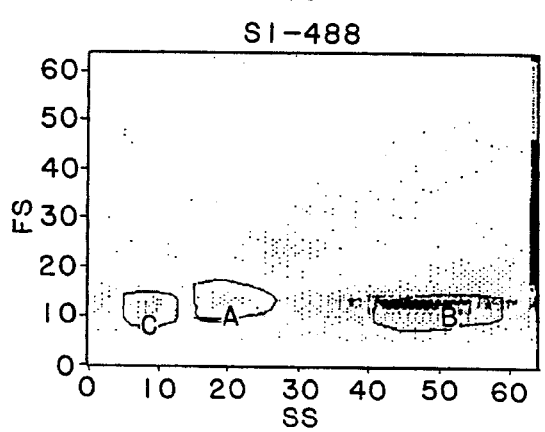
Figure 13C:
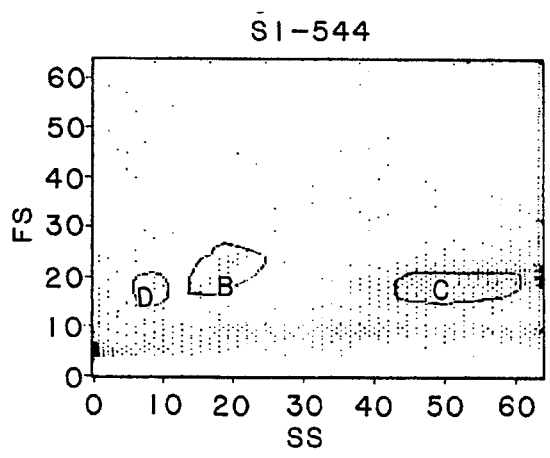
Figure 13D:
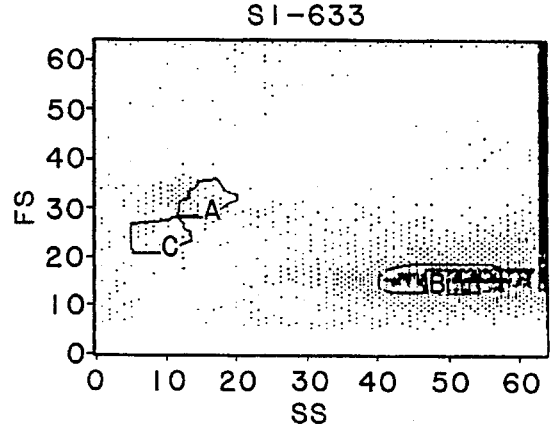
Figure 13E:
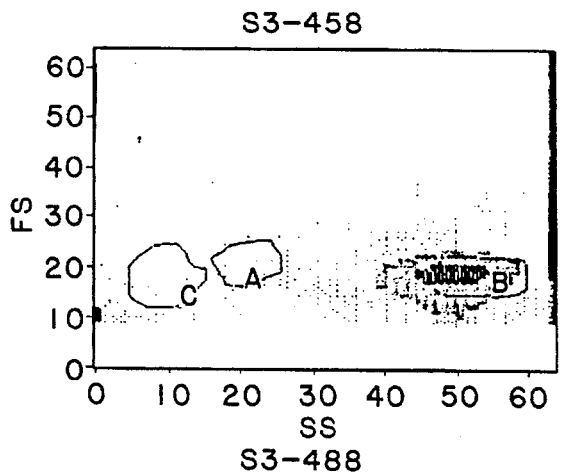
FIGS. 13E–13H illustrate forward versus side scatter in histograms of silver-coated microsphere sample S3 taken at various wavelengths.
Figure 13F:
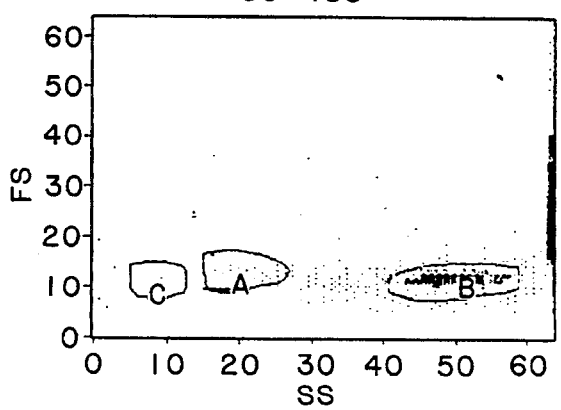
Figure 13G:
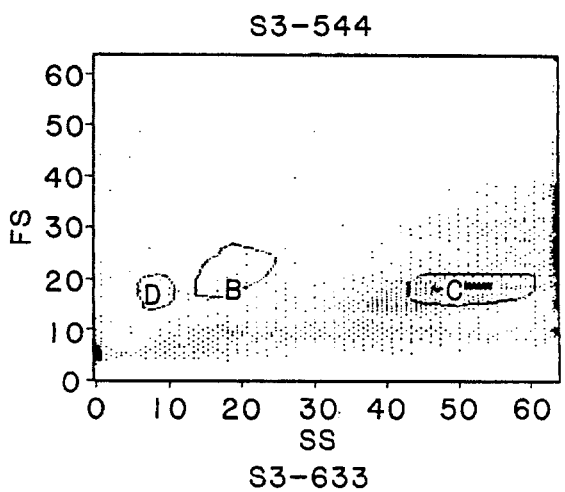
Figure 13H:
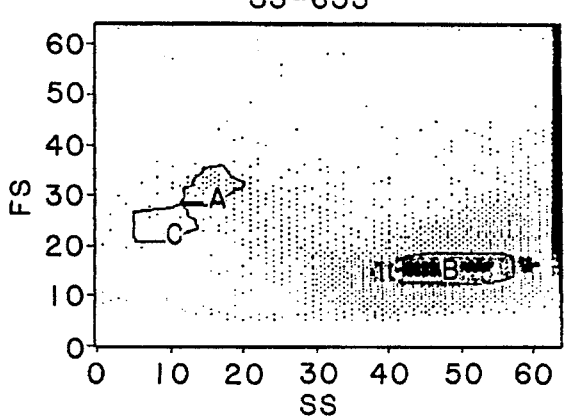
Figure 14A:
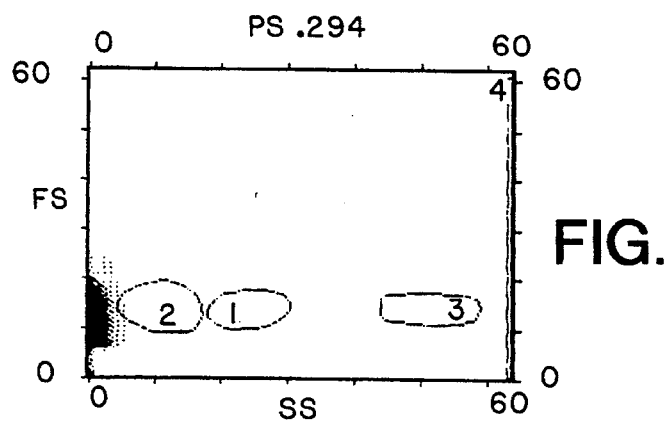
FIGS. 14A–14D illustrate forward versus side scatter in histograms obtained using polystyrene aldehyde/sulfate microspheres (only) of various diameters and 488.0 nm $Ar^+$ laser line excitation.
Figure 14B:
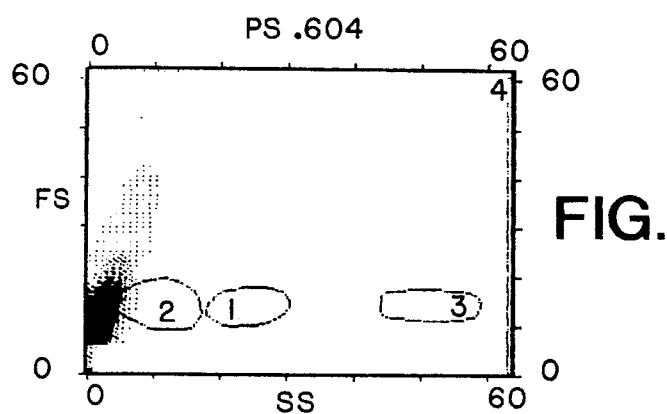
Figure 14C:
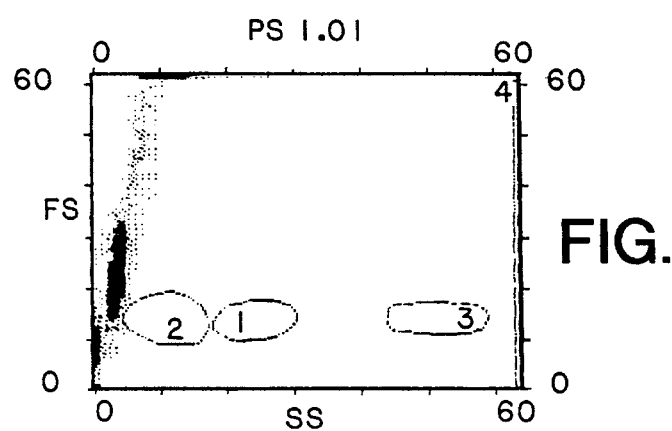
Figure 14D:
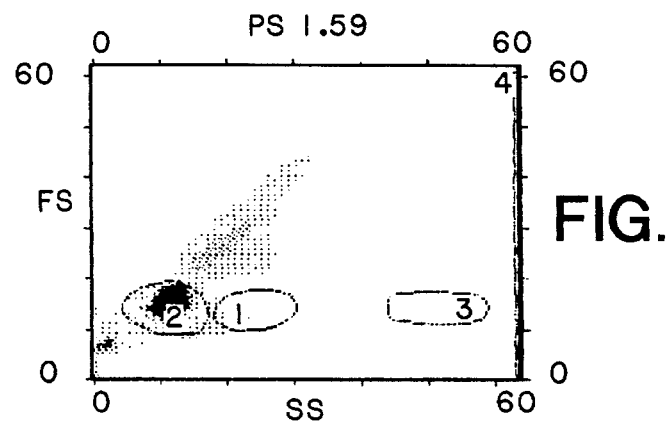
Figure 14E:
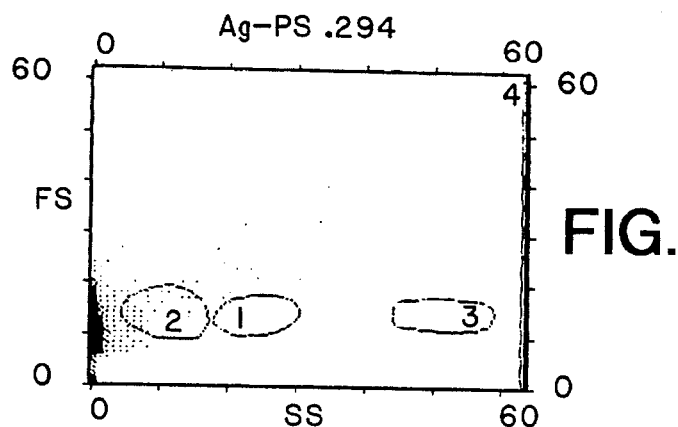
FIGS. 14E–14H, taken using 488.0 nm $Ar^+$ laser line, illustrate forward versus side scatter in histograms of silver-coated particles whose polymeric core sizes correspond to those of FIGS. 12A–12D, respectively.
Figure 14F:
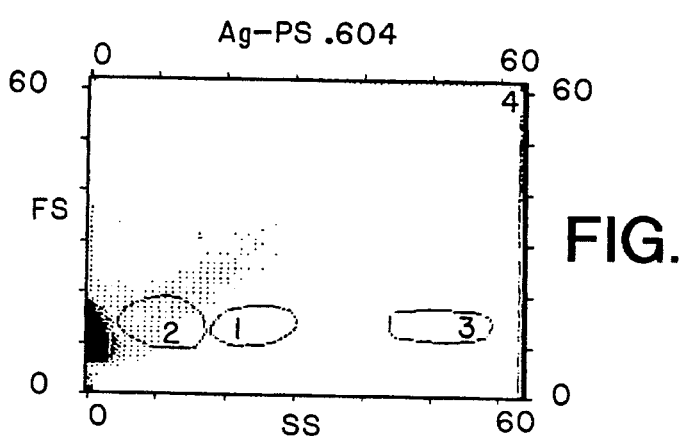
Figure 14G:
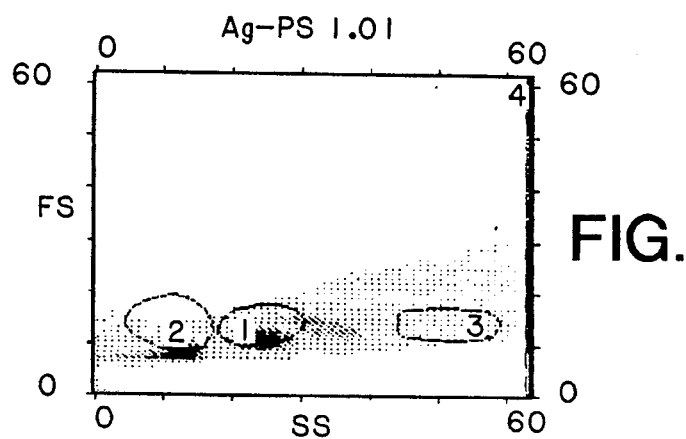
Figure 14H:
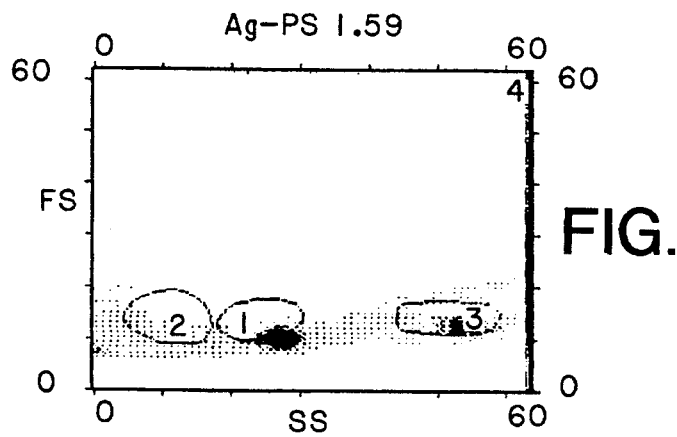
Figure 15A:
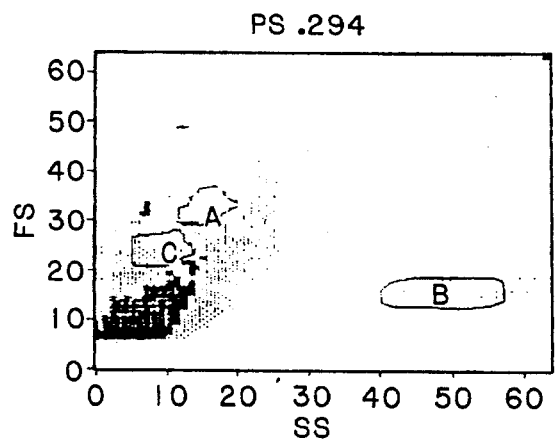
FIGS. 15A–15H correspond to FIGS. 14A–14H, respectively; but were produced using a 632.8 nm He-Ne laser line for excitation.
Figure 15B:
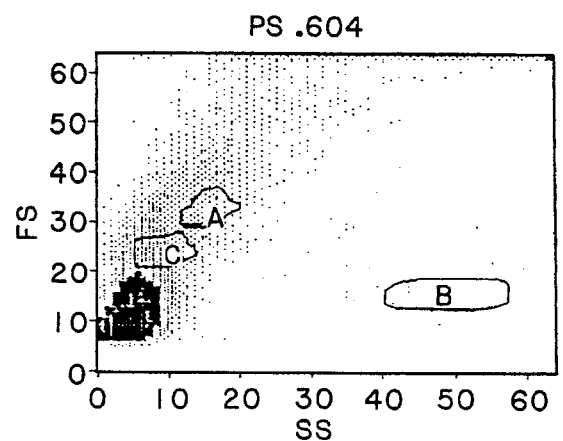
Figure 15C:
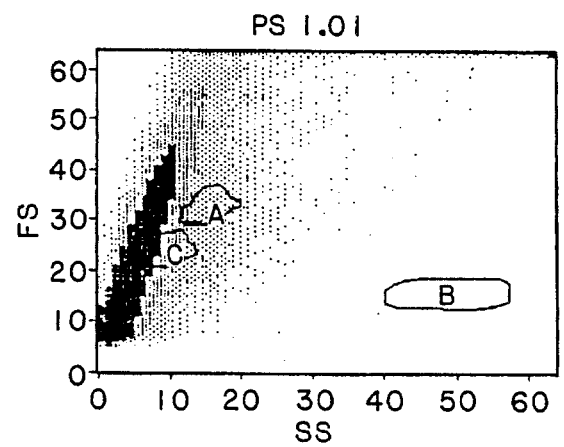
Figure 15D:
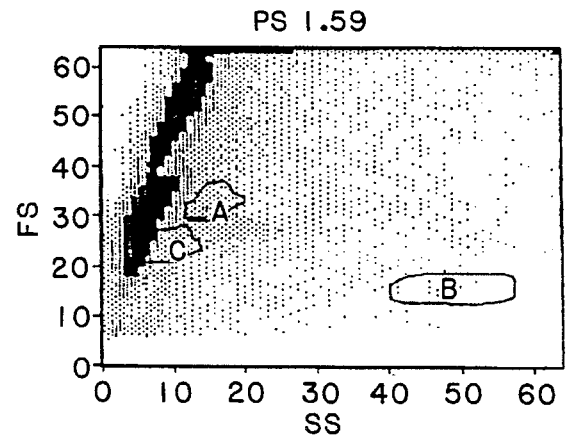
Figure 15E:
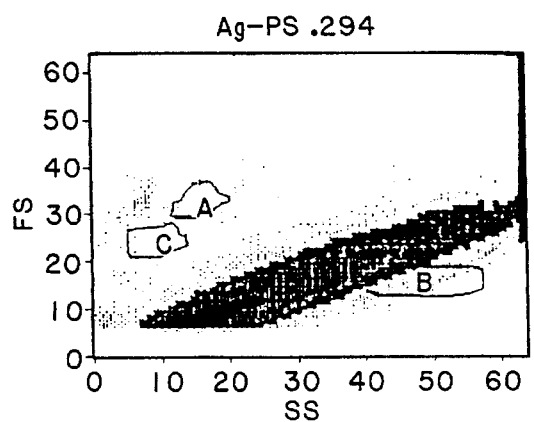
Figure 15F:
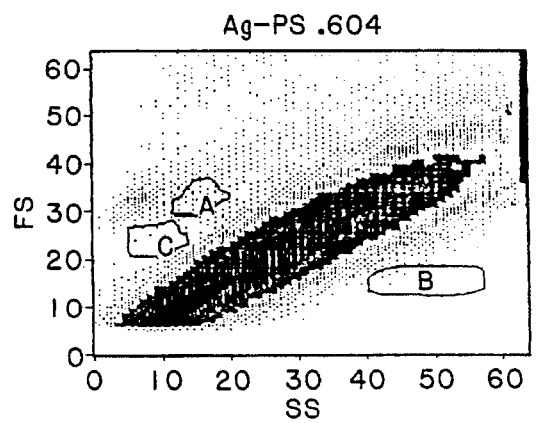
Figure 15G:
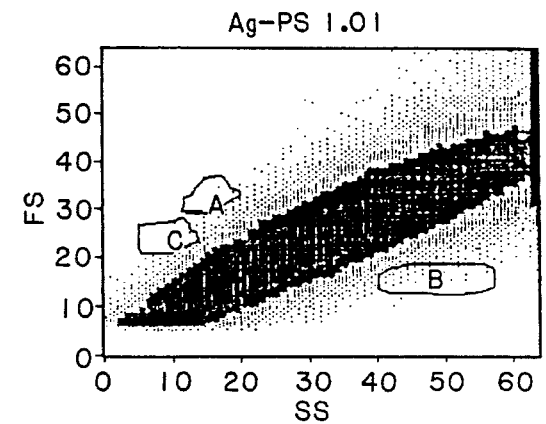
Figure 15H:
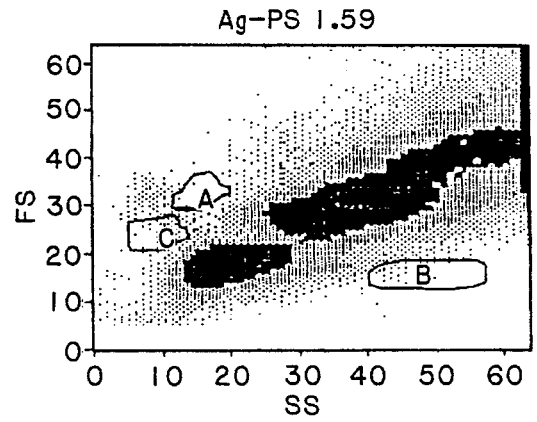

Excitation with 457.9 nm Ar+ (FIGS. 11 and 12) and 544 nm He-Ne laser lines resulted in forward versus side scatter histograms similar to those obtained using the 488.0 nm Ar$^+$ and 632.8 nm He Ne laser lines, respectively. These results confirmed the trends for polystyrene beads with different average size silver or gold structures as obtained using the 488.0 and 632.8 nm laser lines. For example, samples S3 and S1 showed about the same side scatter intensity throughout the 457.9–632.8 nm range (FIGS. 13A–13D). However, as FIGS. 13A–13D illustrate, S1, which has larger silver structures and an extinction maxima at 650 nm, showed progressively greater side scatter as the excitation wavelength increases from 457.9 to 632.8. (Note that the wavelengths in the figure legends are rounded to a whole number. Thus, 457.9 becomes 458 and 632.8 becomes 633). The side scatter for S1 versus S3 is less at 457.9 nm (FIG. 13A vs. FIG. 13D), about the same at 488.0 nm (FIG. 13B vs. FIG. 13F), is greater at 544 nm (FIG. 13C vs. FIG. 13G) and is greater at 632.8 nm (FIG. 13D vs. FIG. 13H). Trial Sample S2, which has smaller sized silver structures than S3, showed consistently less side scatter intensity in the 457.9 to 632.8 nm excitation range than sample S3 (FIGS. 9C and 11C). Sample S4, which has slightly large silver structures than sample S3, showed less side scatter intensity than sample S3 with 457.9 and 488.0 nm excitation, about the same side scatter as S3 with 544 nm excitation and slightly greater side scatter than S3 with 632.8 excitation. Further, when a 351 nm Ar$^+$ multiline source of excitation was used, silver-coated polystyrene bead sample S3 showed no shift in the forward scatter versus side scatter histogram from its position in a histogram of aminodextran (only) coated polystyrene beads.

Silver-coated 0.294 and 0.604 µm polystyrene beads showed no significant shift in light scatter when evaluated using a 488.0 nm Ar laser excitation line. The silver-coated 1.01 and 1.39 µm beads exhibited side scatter shifts to higher intensity, similar to the shifts observed for 2.15 µm silver coated beads. Forward versus side scatter histograms from Coulter Profile® II flow cytometry are shown in FIG. 14. FIGS. 4A–14D were obtained using 5X-Amdex (only) polystyrene beads. FIGS. 14E–14H were obtained using silver coated, 5X Amdex coated polystyrene beads. When using 632.8 nm He-Ne laser excitation, all silver-coated beads of varying sizes exhibited definite side scatter shifts to higher intensity (FIG. 15). Forward scatter was of low intensity and widely spread out for the extensively aggregated, smaller sized silver-coated bead of 0.294 and 0.604 nm diameter.

The above light scattering results obtained by flow cytometry for silver- and gold-coated polystyrene beads are believed to represent the first quantitative verification of the predictions of Lorentz-Mie scattering theory for silver and gold structures in the intermediate, 50 to 200 nm diameter, size range. Those preparations in which the size of colloidal silver or gold structures on polystyrene beads were less than 50 nm and did not give rise to enhanced elastic light scattering in the 457.9 to 632.8 nm excitation region may, nevertheless, produce enormous enhancements of inelastically-scattered light as has been observed in SERS (surface-enhanced Raman scattering) from silver and gold colloidal particles of diameter less than 50 nm. Other, higher order non-linear effects such as enhanced second harmonic generation, four-wave mixing and hyper-Raman scattering may also be observed from the spectra of <50 nm colloidal silver or gold structures on polystyrene.

We claim:

1. Stable colloidal particles suitable for use in instrumental analyses such as flow cytometry or Raman spectroscopy, each such particle comprised of a colloidal-sized core substrate, an aminodextran coating over the peripheral surface of said substrate and a uniform layer of colloidal-sized metallic solid overlaying said aminodextran coating, wherein the metal for said metallic solid is selected from the group consisting of metals which can be reduced from the ionic state to the metal (O) state by the aminodextran coating the core substrate.

2. The particles of claim 1 wherein the metallic solid is selected from the group consisting of metals which form metal ions or metal ion complexes which have a reduction potential of +0.7 volts or higher.

3. The particles of claim 2 wherein said metal is selected from the group consisting of silver and gold.

4. The particles of claim 3 wherein said aminodextran is selected from the group consisting of aminodextrans in which the degree of diamine substitution in said aminodextran is in the range of 1/20–1/5 compared to a maximum theoretical value of 1/2.5.

5. The particles of claim 4 wherein the diamine substitution in said aminodextran is approximately 1/6.

6. The particles of claim 5 wherein the colloidal core substrate is polymeric.

7. The particles of claim 6 wherein the polymer core substrate is polystyrene.

8. The particles of claim 7 wherein the polystyrene core substrate is in the size range 0.2–5.0 microns.

9. The particles of claim 8 wherein the polystyrene core substrate is in the size range 0.2–2.2 microns.

10. The particles of claim 1 wherein said aminodextran is selected from the group consisting of aminodextrans in which the degree of diamine substitution in said aminodextran is in the range of 1/20–1/5 compared to a maximum theoretical value of 1/2.5.

11. The particles of claim 10 wherein the diamine substitution in said aminodextran is approximately 1/6.

12. The particles of claim 1 wherein said colloidal sized core substrate is a polymeric substrate.

13. The particles of claim 12 wherein the polymer core substrate is polystyrene.

14. The particles of claim 13 wherein the polystyrene core substrate is in the size range 0.2–5.0 microns.

15. The particles of claim 14 wherein the polystyrene core substrate is in the size range 0.2–2.2 microns.

16. Stable colloidal particles suitable for use in instrumental analyses such as flow cytometry or Raman spectroscopy, each such particle comprised of a colloidal-sized metallic solid deposited on the peripheral surface of an aminodextran-coated, colloidal-sized core polymeric substrate; said aminodextran being covalently bonded to said core polymeric substrate by a covalent bond between aminodextran amine groups and amine-reactive functional groups on said core polymeric substrate; and said metallic solid and said aminodextran being uniformly dispersed on said peripheral surface, wherein the metal for said metallic solid is selected from the group consisting of metals which can be reduced from the ionic state to the metal (O) state by the aminodextran coating the polymeric core substrate.

17. The particles of claim 16 wherein the metallic solid is selected from the group consisting of metals which form metal ions or metal ion complexes which have a reduction potential of +0.7 volts or higher.

18. The particles of claim 17 wherein the metallic solid is selected from the group consisting of silver and gold.

19. The particles of claim 18 wherein said aminodextran is selected from the group consisting of aminodextrans in which the degree of diamine substitution in said aminodextran is in the range of $1/20$–$1/5$ compared to a maximum theoretical value of $1/2.5$.

20. The particles of claim 19 wherein the diamine substitution in said aminodextran is approximately $1/6$.

21. The particles of claim 20 wherein the polymeric colloidal core substrate is polystyrene.

22. The particles of claim 21 wherein the polystyrene core substrate is in the size range 0.2–5.0 microns.

23. The particles of claim 22 wherein the polystyrene core substrate is in the size range 0.2–2.2 microns.

24. The particles of claim 16 wherein said aminodextran is selected from the group consisting of aminodextrans in which the degree of diamine substitution in said aminodextran is in the range of $1/20$–$1/5$ compared to a maximum theoretical value of $1/2.5$.

25. The particles of claim 24 wherein the degree of diamine substitution in said aminodextran is about $1/6$.

26. The particles of claim 16 wherein the core polymeric substrate is polystyrene.

27. The particles of claim 26 wherein the polystyrene core is in the size range 0.2–5.0 microns.

28. The particles of claim 27 wherein the polystyrene core is in the size range 0.2–2.2 microns.

29. A method of preparing polymeric particles with a uniform coating of a metallic solid on the peripheral surface of said polymeric particles, said method comprising:

(a)(1) adsorbing an aminodextran on the surface of a polymeric colloidal-sized particles, said aminodextran being capable of reducing the metal ion or metal ion complex to the metal (O) state; or (2) covalently binding the aminodextran of (a)(1) to the surface of a polymeric particles;

(b)(1) crosslinking the aminodextran coating of the particles of step (a)(1) by addition of a selected crosslinking agent, or (2) crosslinking the aminodextran coating of the particles of step (a)(2) by the addition of a selected crosslinking agent or optionally not crosslinking said coating;

(c) washing the crosslinked particles of step (b);

(d) mixing together, for a selected reaction time and at a selected reaction temperature, a suspension of the particles of step (c) and a solution of a metal ion or metal ion complex capable of being reduced by the aminodextran coating on the particles of step (c) the reaction time and temperature being sufficient to allow the metal ion or metal ion complex to become coordinated to said aminodextran and subsequently reduced by said aminodextran to the metal (O) state; and (e) separating the metal-coated particles of step (d) and washing the same before using said metal-coated particles.

30. The method of claim 29 wherein said metal ions or metal ion complexes have a reduction potential of +0.7 volts or higher.

31. The method of claim 30 wherein said metal ions or metal ion complexes are selected from the group consisting of silver and gold.

32. The method of claim 29 wherein said polymeric particles are polystyrene microbeads of diameter in the size range 0.2–5.0 microns.

33. The method of claim 32 wherein said polystyrene microspheres are in the size range 0.2–2.2 microns.

34. The method of claim 29 wherein when said metallic solid is silver or gold, said reaction time is in the range of 5 seconds to 10 minutes.

35. The method of claim 29 wherein when said metallic solid is silver or gold, said reaction temperature is in the range of 80°–100° C.

\* \* \* \* \*